(12) United States Patent
Levin et al.

(10) Patent No.: US 10,258,222 B2
(45) Date of Patent: Apr. 16, 2019

(54) MULTI-FOCAL, MULTI-CAMERA ENDOSCOPE SYSTEMS

(71) Applicant: EndoChoice, Inc., Alpharetta, GA (US)

(72) Inventors: Victor Levin, Haifa (IL); Golan Salman, Atlit (IL); Idan Levy, Hadera (IL); Uri David, Ness-Ziona (IL)

(73) Assignee: EndoChoice, Inc., Alpharetta, GA (US)

(*) Notice: Subject to any disclaimer, the term of this patent is extended or adjusted under 35 U.S.C. 154(b) by 653 days.

(21) Appl. No.: 14/805,234

(22) Filed: Jul. 21, 2015

(65) Prior Publication Data

US 2016/0015258 A1    Jan. 21, 2016

Related U.S. Application Data

(60) Provisional application No. 62/029,764, filed on Jul. 28, 2014, provisional application No. 62/027,005, filed on Jul. 21, 2014.

(51) Int. Cl.
*A61B 1/00* (2006.01)
*A61B 1/05* (2006.01)
(Continued)

(52) U.S. Cl.
CPC ........ *A61B 1/00181* (2013.01); *A61B 1/0005* (2013.01); *A61B 1/00006* (2013.01);
(Continued)

(58) Field of Classification Search
CPC ............ A61B 1/00181; A61B 1/00096; A61B 1/00188; A61B 1/00177; A61B 1/00179;
(Continued)

(56) References Cited

U.S. PATENT DOCUMENTS 3,639,714 A    2/1972  Fujimoto
3,955,064 A    5/1976  Demetrio
(Continued)

FOREIGN PATENT DOCUMENTS

CA    2297986    3/1999
CA    2765559   12/2010
(Continued)

OTHER PUBLICATIONS

International Search Report for PCT/US2015/41396, dated Sep. 29, 2015.
(Continued)

*Primary Examiner* — Alexandra L Newton
(74) *Attorney, Agent, or Firm* — Bookoff McAndrews, PLLC

(57) ABSTRACT

A multi-focal, multi-camera endoscope having a tip section including a first optical assembly for generating a first image of a body cavity; a second optical assembly for generating a second image of a body cavity; at least one illuminator associated with each of the first optical assembly and second optical assembly; and a processing system configured to: zoom the first optical assembly and thereby generate a zoomed first image in place of the first image; and automatically cause a physical display to eliminate a display of the second image and to only display said zoomed first image. To eliminate the display of the second image, the processing system reduces a power supply to the second optical assembly, reduces an illumination intensity of an illuminator associated with the second optical assembly or causes the physical display to power off, darken, or blacken.

7 Claims, 23 Drawing Sheets

(51) Int. Cl.
 *G02B 23/24* (2006.01)
 *A61B 1/04* (2006.01)
(52) U.S. Cl.
 CPC ...... *A61B 1/00009* (2013.01); *A61B 1/00177* (2013.01); *A61B 1/00188* (2013.01); *A61B 1/05* (2013.01); *G02B 23/2423* (2013.01); *G02B 23/2484* (2013.01)
(58) Field of Classification Search
 CPC .............. A61B 1/00174; G02B 23/243; G02B 23/2484
 See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | Ebbesmeier nee Schitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0032367 A1* | 3/2002 | Akiba ................ A61B 1/00096 600/127 |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |

(56) References Cited

U.S. PATENT DOCUMENTS

| | | |
|---|---|---|
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |

(56) References Cited

U.S. PATENT DOCUMENTS

| | | |
|---|---|---|
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2011/0306832 A1 | 12/2011 | Bassan et al. |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1* | 10/2012 | Kitano ............... A61B 1/00188 600/109 |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1* | 5/2013 | Levy ..................... A61B 1/042 600/109 |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0178707 A1* | 7/2013 | Kwong ................. A61B 1/227 600/200 |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0142381 A1* | 5/2014 | Bae ..................... A61B 1/00177 600/109 |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |

(56) References Cited

FOREIGN PATENT DOCUMENTS

| | | |
|---|---|---|
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Notice of Allowance dated May 25, 2017 for U.S. Appl. No. 14/318,189.
Office Action dated May 23, 2017 for U.S. Appl. No. 14/500,975.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.

(56) References Cited

OTHER PUBLICATIONS

Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

\* cited by examiner

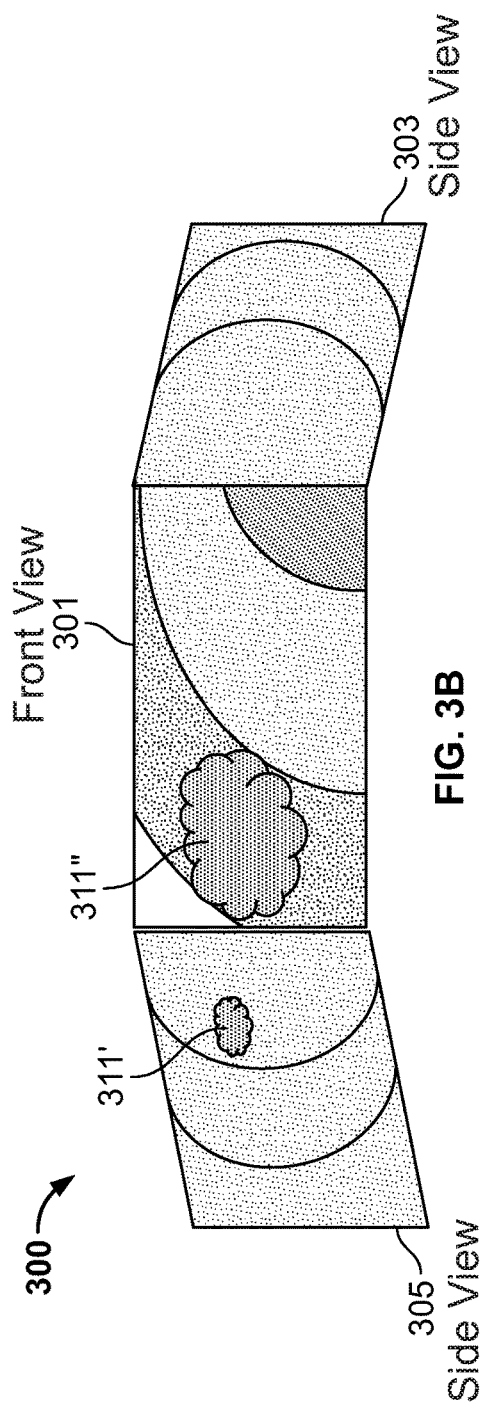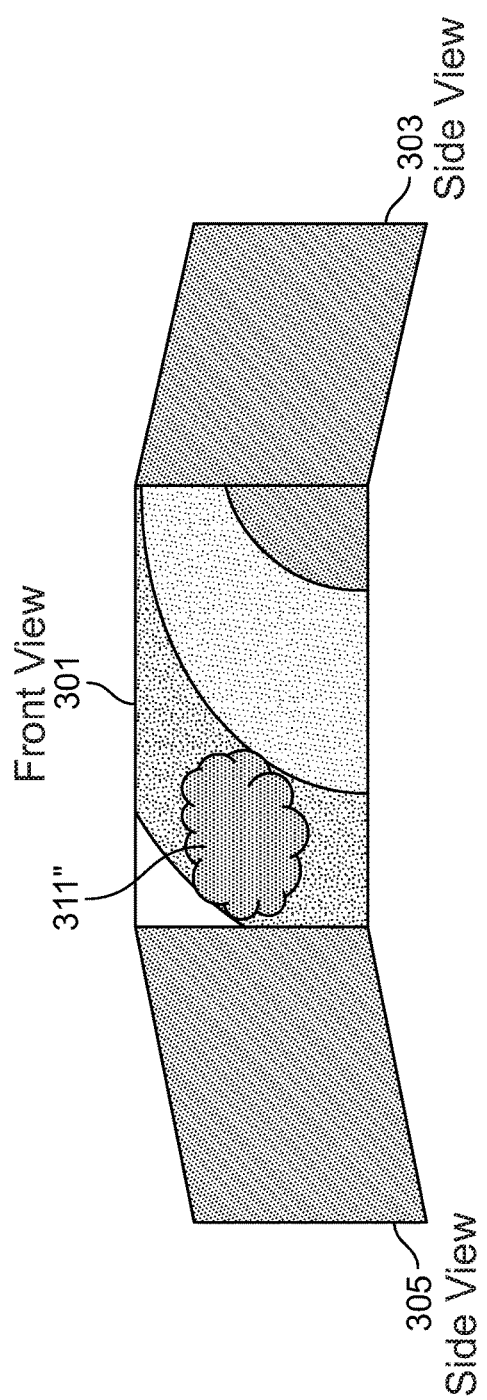
FIG. 3B
FIG. 3C

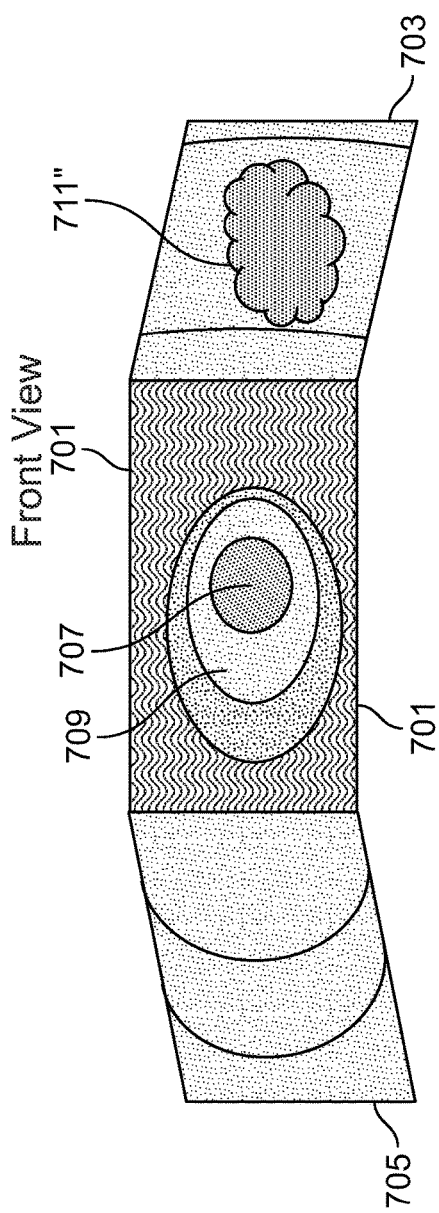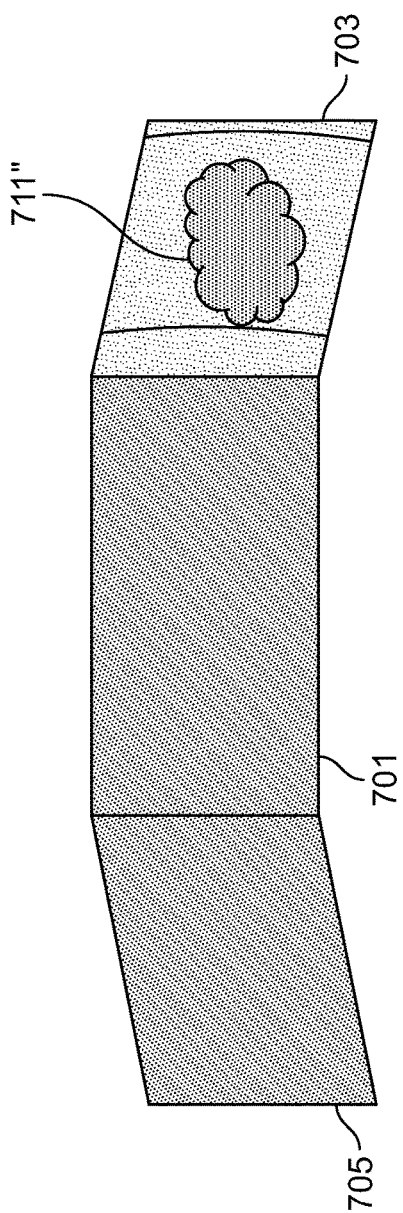

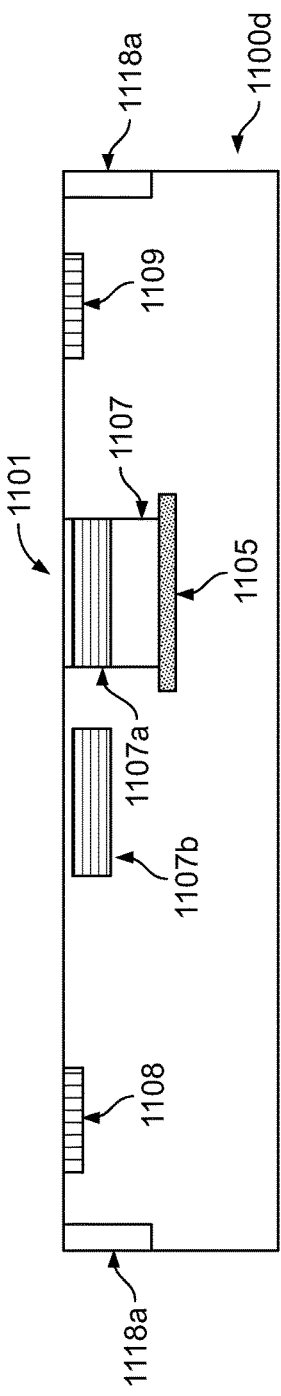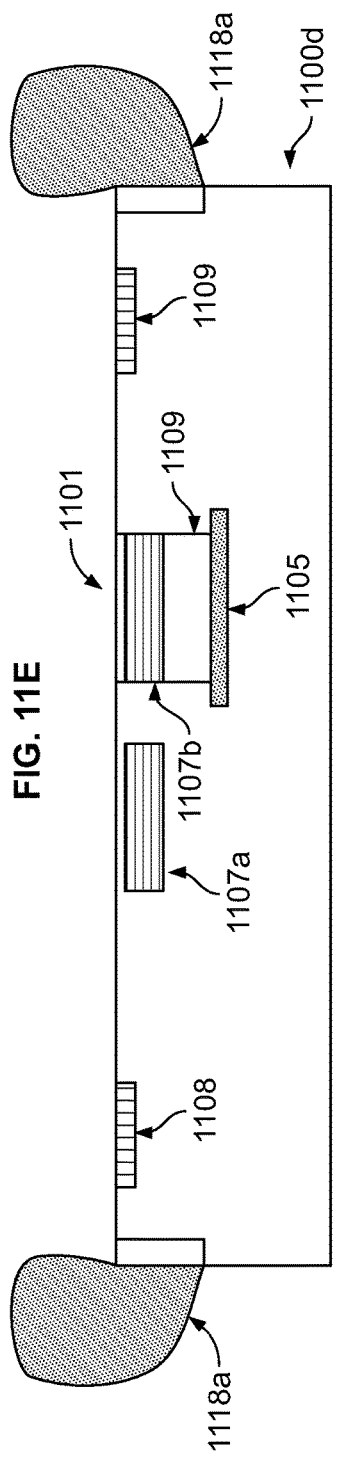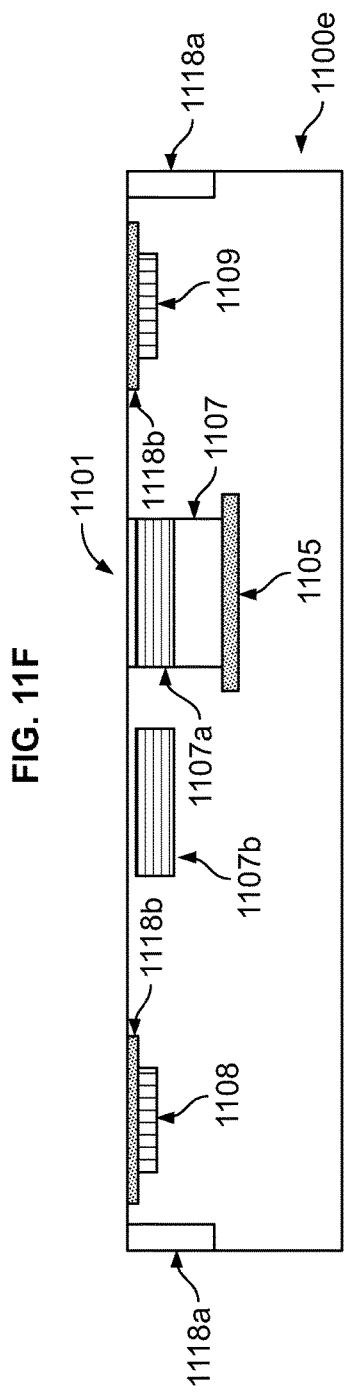

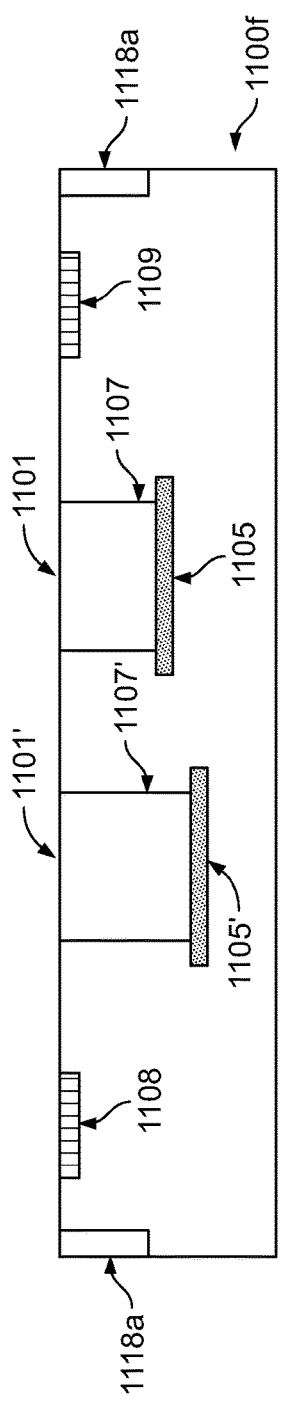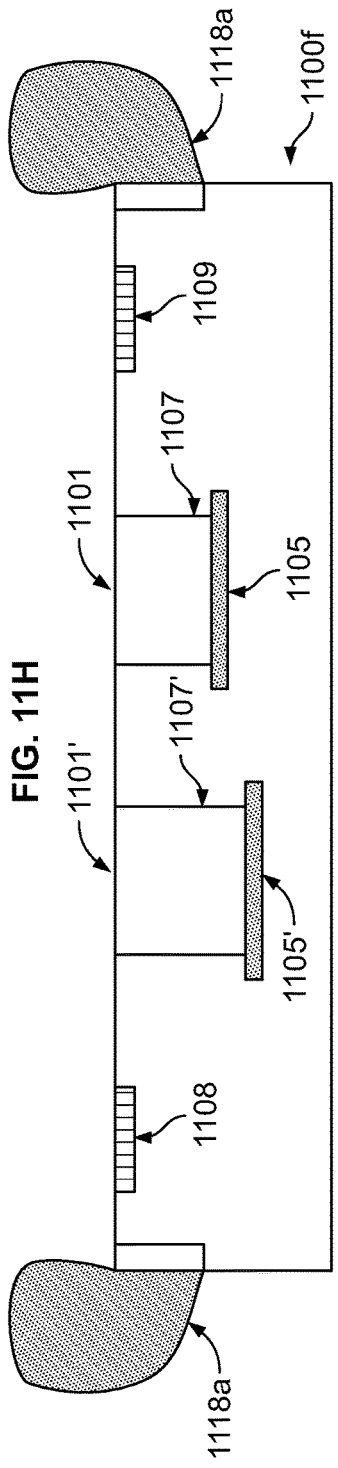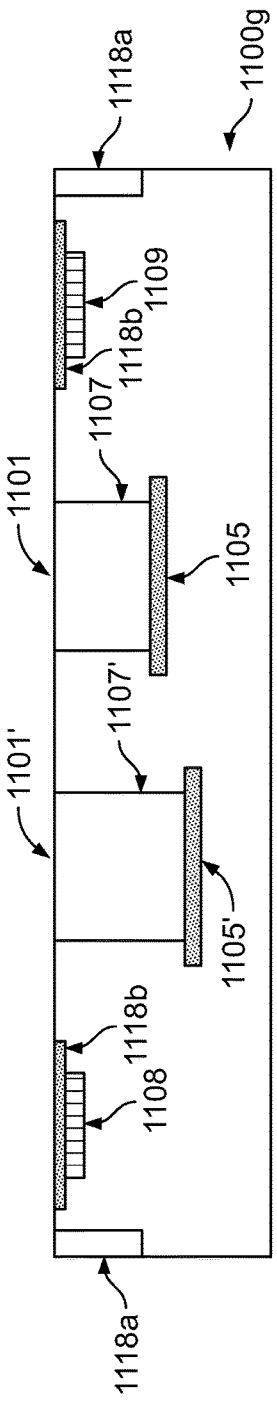

MULTI-FOCAL, MULTI-CAMERA ENDOSCOPE SYSTEMS

CROSS-REFERENCE TO RELATED APPLICATIONS

The present application relies on, for priority, U.S. Patent Provisional Application No. 62/027,005, entitled "Multi-Focal, Multi-Camera Endoscope Systems", filed on Jul. 21, 2014 and U.S. Patent Provisional Application No. 62/029,764, entitled "Multi-Focal, Multi-Camera Endoscope Systems", filed on Jul. 28, 2014 both of which are herein incorporated by reference in their entirety.

FIELD

The present specification relates generally to multi-camera endoscope systems, and in particular to endoscope systems comprising at least one multi-focal optical assembly and/or at least one type of light adjusting components.

BACKGROUND

Some endoscopes, including high resolution endoscopes, are equipped with a lens assembly comprising a movable motor driven lens in the tip of the scope. By controlling the focal distance, the endoscope can move very close to an object of interest, such as a lesion, mucosal, polyp, adenoma and the like, providing a magnified image thereof.

Multi-camera endoscope systems may include a multiple screen display configured to simultaneously display a plurality of images captured by more than one camera. The multi-screen display provides an expanded 330 degrees field of view to the operator that allows identifying, interrogating and treating objects of interest during endoscopic procedures conveniently. U.S. patent application Ser. No. 14/263,896, entitled "Video Processing In a Compact Multi-Viewing Element Endoscope System" and filed on Apr. 28, 2014 is herein incorporated by reference in its entirety. In addition, U.S. patent application Ser. No. 14/273,923, entitled "Operational Interface In A Multi-Viewing Elements Endoscope", and filed on May 9, 2014 is also herein incorporated by reference in its entirety. In addition, the present specification is related to U.S. patent application Ser. No. 13/882,004, entitled "Optical Systems for Multi-Sensor Endoscopes", and filed on Apr. 26, 2013, which is herein incorporated by reference in addition to the priority applications upon which it relies.

However, zooming in and magnifying an object image by a predetermined percentage, which may be over about 30% for example, while other objects are displayed with a lower magnification on a multi-screen display, may cause loss of visual orientation, visual fatigue and is generally an uncomfortable experience for the operator.

Moreover, the inclusion of one or more lens assemblies, each comprising a movable motor driven lens, requires significant space which is an extremely limited resource at the tip section of a multi-camera endoscope.

Thus, it would be highly advantageous to provide a multi-focal, multi-camera endoscope systems that may be used to comfortably identify and magnify objects of interest during endoscopic procedures, while still being small and compact enough to fit within the limited volume of an endoscope tip.

SUMMARY

In some embodiments, the present specification discloses a tip section of an endoscope, comprising: a first optical assembly for generating a first image of a body cavity; a second optical assembly for generating a second image of a body cavity; at least one illuminator associated with each of the first optical assembly and second optical assembly; and a processing system configured to: zoom the first optical assembly and thereby generate a zoomed first image in place of the first image; and automatically cause a physical display to eliminate a display of the second image and to only display said zoomed first image.

Optionally, the tip section is part of an endoscope system and further comprises at least two screens for respectively displaying the first image and the second image.

In some embodiments, the at least one illuminator is sufficiently proximate such that it is the primary illuminator of the field of view of the associated optical assembly.

Optionally, the first image may overlap with the second image. Still optionally, the first image may not overlap with the second image. Optionally, "overlap" may be defined as capturing a view of the same physical object.

Optionally, to eliminate the display of the second image, the processing system reduces a power supply to the second optical assembly.

Optionally, to eliminate the display of the second image, the processing system reduces an illumination intensity of said at least one illuminator associated with the second optical assembly.

Optionally, to eliminate the display of the second image, the processing system causes the physical display to power off, darken, or blacken.

In some embodiments, the first optical assembly may be a front-pointing optical assembly and the second optical assembly may be a first side-pointing optical assembly.

Optionally, the tip section further comprises a third optical assembly for generating a third image of the body cavity and displaying said third image on a corresponding third screen, wherein the third optical assembly is a second side-pointing optical assembly.

Optionally, at least one of the first and second optical assemblies is configured to operate at a first working distance and a second working distance. Still optionally, said zoomed image is created when said at least one optical assembly is switched from said first working distance to said second working distance. Still optionally, said first working distance provides magnification ranging between 100× to 6×. Still optionally, said second working distance provides magnification ranging between 250× to 100×.

In some embodiments, the present specification discloses a method of using an endoscope having a tip section with at least two optical assemblies and at least one illuminator associated with each of said at least two optical assemblies, the method comprising: generating at least two images of a body cavity from each of said at least two optical assemblies; displaying a first image and a second image of the at least two images on a first screen and a second screen, respectively; zooming one of said at least two optical assemblies to generate and display a zoomed image in place of the first image of the at least two images; and automatically eliminating a display of the second image of the at least two images on the second screen.

Optionally, eliminating the display of the second image of the at least two images is performed by reducing a power supply to the optical assembly generating the second image of the at least two images.

Optionally, eliminating the display of the second image of the at least two images is enabled by reducing an illumination intensity of said at least one illuminator associated with the optical assembly generating the second image of the at least two images.

Optionally, eliminating the display of the second image of the at least two images is enabled by powering off, darkening, or blackening one of said at least two screens corresponding to the display of the second image of the at least two images.

Optionally, a first of said at least two optical assemblies is a front-pointing optical assembly and a second of said at least two optical assemblies is a first side-pointing optical assembly.

In some embodiments, the endoscope may further comprise a third optical assembly for generating a third image of the body cavity and displaying said third image on a corresponding third screen, wherein the third optical assembly is a second side-pointing optical assembly.

Optionally, at least one of said at least two optical assemblies is configured to operate at a first working distance and a second working distance. Still optionally, said zoomed image is created when said optical assembly is switched from said first working distance to said second working distance. Still optionally, said first working distance provides magnification ranging between 100× to 6×. Still optionally, said second working distance provides magnification ranging between 250× to 100×.

In some embodiments, the present specification discloses an endoscope system having an endoscope tip comprising: a front pointing optical assembly for generating a first image of a body cavity at a first working distance and a second image at a second working distance, wherein the front optical assembly comprises a front lens assembly mounted on a front image sensor and wherein said front lens assembly includes a first lens associated with said first working distance and a second lens associated with said second working distance; at least one side pointing optical assembly for generating at least one side image of the body cavity; at least one illuminator associated with each of said front pointing optical assembly and said at least one side pointing optical assembly; at least one actuation element located within said front pointing optical assembly; and a processing system configured to enable said at least one actuation element to: move said first lens out of an optical path that connects a line of sight from said front image sensor to an object of interest within said body cavity; and move said second lens into said optical path to generate said second image.

Optionally, said first image generated at said first working distance has magnification in a range between 100× to 6×. Optionally, said second image generated at said second working distance has magnification in a range between 250× to 100×.

Optionally, said at least one actuation element comprises at least one pneumatic engine. Optionally, said at least one actuation element comprises a piezoelectric element, an electric engine, solenoid, a Nitinol engine, a pneumatic engine, or a combination thereof.

Optionally, said endoscope system comprises a front screen and at least one side screen, wherein the front screen is configured to display said first or second image and the at least one side screen is configured to display said at least one side image.

In some embodiments, upon moving said second lens into the optical path, the processing system may further be configured to automatically eliminate the display of said at least one side image.

Optionally, the processing system eliminates the display of said at least one side image by cutting off or reducing a power supply to the at least one side pointing optical assembly.

Optionally, the processing system eliminates the display of said at least one side image by powering off or reducing an illumination intensity of said at least one illuminator associated with said at least one side pointing optical assembly.

Optionally, wherein the processing system eliminates the display of said at least one side image by powering off, darkening or blackening said at least one side screen.

In some embodiments, the present specification discloses, a tip section of an endoscope, comprising: a front pointing optical assembly for generating a front image of a body cavity; a first side pointing optical assembly for generating a first image of the body cavity at a first working distance and a second image at a second working distance, wherein the first side optical assembly comprises a first side lens assembly mounted on a first side image sensor and wherein said first side lens assembly includes a first lens associated with said first working distance and a second lens associated with said second working distance; one or more illuminators associated with each of said front pointing optical assembly and said first side pointing optical assembly; one or more actuation elements located within said first side lens assembly; and a processor configured to enable said one or more actuation elements to: move said first lens out of an optical path that connects a line of sight from said first side image sensor to an object of interest within said body cavity; and move said second lens into the optical path to enable generating said second image.

Optionally, wherein said first image generated at said first working distance has a magnification ranging between 100× to 6×. Still optionally, said second image generated at said second working distance has a magnification ranging between 250× to 100×.

Optionally, said one or more actuation elements comprise at least one pneumatic engine. Still optionally, said one or more actuation elements may comprise any one or a combination of a piezoelectric element, an electric engine, solenoid, a Nitinol engine, at least one pneumatic engine.

Optionally, the processor is configured to display said front image on a front screen and display said first or second image on a first side screen.

In some embodiments, upon moving said second lens into the optical path, the processor may further be configured to automatically eliminate display of said front image.

Optionally, the processor is configured to eliminate the display of said front image by powering off or reducing a power supply to the front pointing optical assembly.

Optionally, the processor is configured to eliminate the display of said front image by powering off or reducing an illumination intensity of said one or more illuminators associated with said front pointing optical assembly. Optionally, the processor is configured to eliminate the display of said front image by powering off, darkening or blackening said front screen.

In some embodiments, the present specification discloses a tip section of an endoscope, comprising: a front pointing optical assembly for generating a first image of a body cavity at a first working distance and a second image at a second working distance; at least one side pointing optical assembly for generating at least one side image of the body cavity; one or more illuminators associated with each of said front pointing optical assembly and said at least one side pointing optical assembly; one or more spacers retractably positioned at a distal end of the tip section; and a processing system configured to enable said one or more spacers to be deployed in an extended position to maintain a distance between said front pointing optical assembly and a wall of said body cavity and to be retracted back into the distal end of the tip section.

Optionally, said distance approximately matches said second working distance.

Optionally, a protruding length of said one or more spacers each ranges between 1.5 to 7 millimeters.

Optionally, one or more spacers are positioned such that a distance between any two of said spacers ranges between 8 to 10 millimeters.

Optionally, said first image generated at said first working distance has magnification in a range between 100× to 6×, and wherein said second image generated at said second working distance has magnification in a range between 250× to 100×.

In some embodiments, the present specification discloses a tip section of an endoscope, comprising: a front pointing optical assembly for generating a front image; a first side pointing optical assembly for generating a first image at a first working distance and a second image at a second working distance; one or more illuminators associated with each of said front and side pointing optical assembly; three or more spacers retractably mounted at a distal end of the tip section and associated with said first side pointing optical assembly; and a processor configured to enable said three or more spacers to be deployed in an extended position to maintain a distance between said first side pointing optical assembly and a wall of said body cavity in order to generate said second image and to retract said three or more spacers back into the distal end of the tip section.

Optionally, said distance approximately matches said second working distance.

Optionally, a radially protruding height of said three or more spacers ranges between 1.5 to 7 millimeters.

Optionally, three or more spacers are positioned such that a distance between any two of said consecutive spacers ranges between 8 to 10 millimeters.

Optionally, said first image generated at said first working distance has a magnification ranging between 100× to 6×, and wherein said second image generated at said second working distance has magnification ranging between 250× to 100×.

In some embodiments, the present specification discloses a tip section of an endoscope, comprising: at least one optical assembly for generating a first image of a body cavity at a first working distance and a second image at a second working distance, wherein said second working distance is shorter than said first working distance; one or more illuminators associated with said at least one optical assembly and configured to provide a first mode of illumination associated with said first working distance and a second mode of illumination associated with said second working distance; first and second light adjusting components retractably positioned on either side of said at least one optical assembly such that said optical assembly and said one or more illuminators lie between said first and second light adjusting components; third and fourth light adjusting components mounted on said one or more illuminators, wherein said third and fourth light adjusting components allow a passage of light during said first mode of illumination and diffuse light during said second mode of illumination; and a processor configured to perform any one or both of the following: enable said first and second light adjusting components to be deployed when said at least one optical assembly is configured to generate said second image at said second working distance, wherein deployment of said first and second light adjusting components cause said first mode of illumination to be modified to said second mode of illumination; enable said third and fourth light adjusting components to diffuse light when said at least one optical assembly is configured to generate said second image at said second working distance.

Optionally, said first and second light adjusting components have lamebrain reflectance surfaces.

Optionally, said first and second light adjusting components are balloons that are inflated for deployment.

Optionally, said third and fourth light adjusting components are liquid crystal transmissive screens.

Optionally, a size of said first and second light adjusting components, when deployed, approximately matches said second working distance.

Optionally, said first image generated at said first working distance has a magnification ranging between 100× to 6×. Still optionally, said second image generated at said second working distance has a magnification ranging between 250× to 100×.

Optionally, said first mode of illumination is characterized by a field of illumination of said one or mode illuminators ranging between 150° and 170° with rays of illumination falling directly on an anomaly within the body cavity. Optionally, said second mode of illumination is characterized by a field of illumination of said one or mode illuminators ranging between 140° and 180° with oblique rays of illumination falling on an anomaly within the body cavity.

Optionally, said first working distance ranges between 4 to 100 millimeters and said second working distance ranges between 1 to 4 millimeters.

In some embodiments, the present specification discloses a method of using a tip section of an endoscope having at least one optical assembly, one or more associated illuminators and first, second, third and fourth light adjusting components, wherein the first and second light adjusting components are retractably positioned on either side of said at least one optical assembly such that said optical assembly and said one or more illuminators lie between said first and second light adjusting components and wherein the third and fourth light adjusting components are mounted on said one or more illuminators, the method comprising: using the at least one optical assembly to generate a first image of a body cavity at a first working distance, while the first and second light adjusting components are in retracted configuration and the third and fourth light adjusting components allow passage of light from said one or more illuminators during a first mode of illumination; and using the at least one optical assembly to generate a second image at a second working distance, and performing any one or both of the following: deploying said first and second light adjusting components thereby modifying said first mode of illumination of said one or more illuminators to a second mode of illumination; enabling said third and fourth light adjusting components to diffuse light thereby modifying said first mode of illumination of said one or more illuminators to said second mode of illumination.

Optionally, said first and second light adjusting components have lamebrain reflectance surfaces. Optionally, said first and second light adjusting components are balloons that are inflated for deployment.

Optionally, said third and fourth light adjusting components are liquid crystal transmissive screens.

Optionally, a size of said first and second light adjusting components, when deployed, approximately matches said second working distance.

Optionally, said first image generated at said first working distance has magnification ranging between 100× to 6×. Optionally, said second image generated at said second working distance has magnification ranging between 250× to 100×.

Optionally, said first mode of illumination is characterized by a field of illumination of said one or mode illuminators ranging between 150° and 170° with rays of illumination falling directly on an anomaly within the body cavity.

Optionally, said second mode of illumination is characterized by a field of illumination of said one or mode illuminators ranging between 140° and 180° with oblique rays of illumination falling on an anomaly within the body cavity.

Optionally, said first working distance ranges between 4 to 100 millimeters and said second working distance ranges between 1 to 4 millimeters.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 3B is the multi-camera display system of FIG. 3A with a front view screen displaying a magnified image of an anomaly identified by a multi-focal front-pointing optical assembly;

FIG. 3C is the multi-camera display system of FIG. 3B with presentations on first and second side view screens disabled or darkened;

FIG. 7B is the multi-camera display system of FIG. 7A with a first-side view screen displaying a magnified image of an anomaly identified by a multi-focal first side-pointing optical assembly;

FIG. 7C is the multi-camera display system of FIG. 7B with presentations on front and second side view screens disabled or darkened;

FIG. 11E illustrates an endoscope tip section with another embodiment of a multi-focal optical assembly in a first mode of operation and the first type of light adjusting components refracted in the first mode of illumination;

FIG. 11F illustrates the endoscope tip section of FIG. 11E with the multi-focal optical assembly in the second mode of operation and the first type of light adjusting components deployed in the second mode of illumination;

FIG. 11G illustrates an endoscope tip section with a multi-focal optical assembly in the first mode of operation and first and second types of light adjusting components in the first mode of illumination;

FIG. 11H illustrates an endoscope tip section with an embodiment of a composite multi-focal optical assembly in the first mode of operation and the first type of light adjusting components refracted in the first mode of illumination;

FIG. 11I illustrates the endoscope tip section of FIG. 11H with the composite multi-focal optical assembly in the second mode of operation and the first type of light adjusting components deployed in the second mode of illumination;

FIG. 11J illustrates an endoscope tip section with a multi-focal composite optical assembly in the first mode of operation and first and second types of light adjusting components in the first mode of illumination;

DETAILED DESCRIPTION

Figure 1:
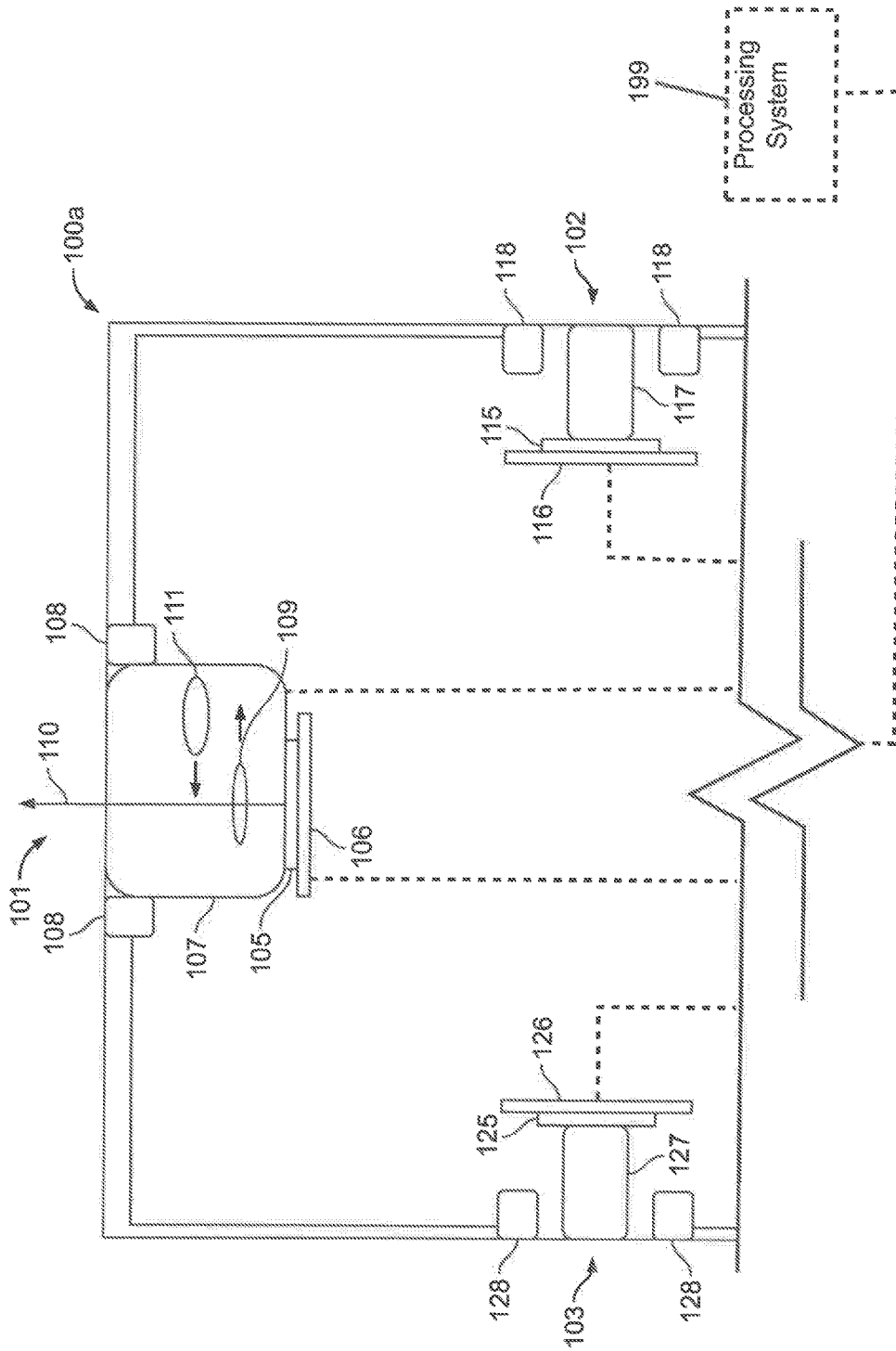
FIG. 1 is a cross-section view of a multi-camera endoscope tip section having a multi-focal front-pointing optical assembly, in accordance with an embodiment.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present specification.

In the description and claims of the application, each of the words "comprise" "include" and "have", and forms thereof, are not necessarily limited to members in a list with which the words may be associated.

According to aspects and embodiments of the present invention, multi-focal (for example, dual focus) multi-camera endoscope systems are disclosed. The endoscope system, according to some embodiments, includes at least one multi-focal optical assembly comprising at least one image sensor and at least one lens assembly further comprising optical element(s) configured to shift from a first working distance to a second working distance, when triggered by a processor associated with the endoscope system, thereby to provide an increased magnification of an object of interest.

As used herein in accordance with some embodiments, at least the lens assembly is part of a "camera" or "viewing element". In some embodiments, the term 'camera' is used to describe a lens assembly and its associated image sensor. The "camera" or "viewing element" with associated image sensor and associated circuit board form an "optical assembly". Further, the optical assembly typically is associated with at least one illuminator for illuminating the field of view. Thus, a multi-focal optical assembly includes a multi-focal viewing element with associated sensor, associated circuit board and is associated with at least one illuminator, in various embodiments. In various other embodiments, the multi-focal optical assembly is also associated with at least one of first and second types of light adjusting components configured to function in a first or a second mode of illumination. Throughout this specification, the terms "camera" and "viewing element" are used interchangeably.

In some embodiments, a processing system is employed, wherein said processing system includes a processor in operation with local or remote memory and other electronic components known to persons of ordinary skill in the art.

In some embodiments, portions of the present invention may be implemented as a plurality of software instructions executed by a data processor, for example, which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more input devices (e.g., allowing input of commands and/or parameters) and output devices (e.g., allowing reporting parameters of operation and results).

Multi-camera endoscope systems also include a multi-screen display configured to display simultaneously a plurality of images captured by more than one optical assembly. However, zooming in and magnifying an image by a pre-determined percentage, which may be over about 30% for example, while other images are displayed with a lower magnification on such multi-image display, may cause a loss of visual orientation and generally a visual fatigue and discomfort experience to the operator. Hence, according to aspects and embodiments of the present specification, the processor is configured to allow the operator to focus only on the magnified image of interest obtained from one optical assembly (which is a multi-focal optical assembly) by disabling other optical assemblies, the associated illumination and/or presentation of images obtained from the other optical assemblies or any combination thereof.

Thus, in order to enable the operator to focus only on the magnified image of interest obtained from a multi-focal optical assembly, the processor is configured to enable any one or a combination of the following actions: a) switch off the other optical assemblies capturing the lower magnification images while one or more illuminators associated with the other optical assemblies continue to stay switched on and the screens displaying the lower magnification images also continue to remain switched on, b) switch off the one or more illuminators associated with the other optical assemblies while the other optical assemblies continue to capture and generate live images and/or video and the screens displaying the lower magnification images also continue to remain switched on, and/or c) switch off, darken or blacken the screens displaying the lower magnification images while the other optical assemblies continue to capture and generate live images and/or video and the one or more illuminators associated with the other optical assemblies also continue to stay switched on.

Reference is now made to FIG. 1, which shows a cross section of a multi-focal, multi-camera endoscope tip section, according to certain embodiments. Endoscope tip section 100a includes a multi-focal front-pointing optical assembly 101 positioned at a distal end of an endoscope, such as a colonoscope. Front-pointing optical assembly 101 typically has a wide field of view of 170 degrees. The endoscope tip section 100a includes a first side-pointing optical assembly 102 and a second side pointing optical assembly 103. The two side-pointing optical assemblies 102 and 103 and the multi-focal front-pointing optical assembly 101 are configured to provide an expanded field of view of about 330 degrees. In various embodiments, the first and second side-pointing optical assemblies 102, 103 are positioned such that their optical axes are at a distance ranging between 6 mm and 10 mm from the distal end of the endoscope. The front-pointing, first and second side-pointing optical assemblies 101, 102, 103 each have a field of view (FOV) ranging between 150 to 170 degrees, in various embodiments.

While the multi-focal front-pointing optical assembly 101 is able to detect objects of interest, such as polyps, visible in the front field of view, side-pointing optical assemblies 102 and 103 are further able to detect objects of interest, which may be hidden from the front-pointing optical assembly 101, for example in inner side of folds of a colon. According to some embodiments, a focal length of the front-pointing optical assembly 101 is on the order of 1.1 mm while that of the first and second side-pointing assemblies 102, 103 is on the order of 1.0 mm.

The multi-focal front-pointing optical assembly 101 includes a front-pointing viewing element or camera having a front-pointing image sensor 105 such as Charge Coupled Device (CCD) or a Complementary Metal Oxide Semiconductor (CMOS) image sensor. The front-pointing image sensor 105 has a lens assembly 107 mounted on top of it for providing the necessary optics for receiving images. The lens assembly 107 includes a plurality of lenses, static or movable, which provide a field of view of at least 90 degrees and up to essentially 180 degrees.

The front-pointing image sensor 105 is mounted on an integrated circuit board 106, which may be rigid or flexible. The integrated circuit board 106 supplies the front-pointing image sensor 105 with necessary electrical power, and derives still images and/or video feeds captured by the image sensor 105. The integrated circuit board 106 is connected to a set of electrical cables which are threaded through an electrical channel running through an elongated shaft of the endoscope.

One or more discrete front illuminators 108 are placed next to the lens assembly 107, for illuminating its field of view. Optionally, discrete front illuminators 108 may be attached to the same integrated circuit board 106 on which front-pointing image sensor 105 is mounted. Thus, in some embodiments, the multi-focal front-pointing optical assembly 101, includes at least a front-pointing viewing element which comprises lens assembly 107 and front-pointing image sensor 105, mounted on integrated circuit board 106, and associated with at least one illuminator 108.

In one embodiment, the illuminators are optionally discrete illuminators and include a light-emitting diode (LED). Thus, light is provided by light emitting diodes (LED) that illuminates the fields of view. According to some embodiments, white light LEDs are used. According to other embodiments, other colors of LEDs or any combination of LEDs may be used, including but not limited to red, green, blue, infrared, near infrared and ultraviolet or any other LED.

The term "discrete", concerning discrete illuminator, refers to an illumination source, which generates light internally, in contrast to a non-discrete illuminator, which may be, for example, a fiber optic merely transmitting light generated remotely.

In some embodiments, the light may be generated internally within the endoscope tip section 100a, or generated remotely and transferred, for example, by a fiber optic. In some embodiments, two or more illuminators may be employed, wherein at least one may generate the light internally, and at least one may provide remotely generated light.

According to some embodiments of the present specification, the lens assembly 107 includes two lenses 109 and 111 that are switched dynamically by a processor 199, associated with the endoscope, in order to shift from a first working distance (associated with the first lens 109) to a second working distance (associated with the second lens 111) to increase image magnification of an anomaly, such as a polyp for example, captured by the multi-focal front-pointing optical assembly 101 and its associated components.

According to aspects and embodiments of the present specification, shifting from the first working distance to the second working distance allows for increased magnification and an improved image that can be generated by the image sensor 105. Shifting to the second working distance allows using the lens 111 with improved modulation transfer function (MTF) and aberration qualities adapted to a shorter depth of field (DOF) compared to the longer DOF of the first regular lens 109. For example, the first working distance and DOF of the first lens 109 is about 3 to 100 millimeters (mm) while the second working distance and DOF of the second lens 111 is about 2 to 5 mm or about 2 to 7 mm. The imaging performance provided by the second lens 111, adapted to shorter distances, is superior at these short distances compared to the imaging performance of the regular first lens 109, having typically 3 to 100 mm DOF, where a camera shutter is used to limit the field of view at short distances, thereby providing lower resolution and reduced light intensity.

In various alternate embodiments, the first working distance is about 6 to 70 mm, while the second working distance is about 2 to 4 mm.

In accordance with aspects of the present specification, the lens assembly 107 includes one or more actuation elements configured to control optical elements included in the lens assembly 107. The one or more actuation elements comprise a pneumatic engine, a piezoelectric element, an electric engine, solenoid, a Nitinol engine or any combination thereof. In a preferred embodiment, the actuation elements comprise at least one pneumatic engine. The optical elements comprise lenses (such as lenses 109, 111), mirrors, diffraction elements or any combination thereof.

In various embodiments, the actuation elements are triggered by the processor 199 to push, move or pull lens 109 out of the optical path 110 and push, move or pull lens 111 onto the optical path 110 such that the optical path 110 that connects the line of sight from image sensor 105 to a target pass through first lens 109 or second lens 111.

In accordance with various embodiments, the endoscope tip section 100a includes a first side-pointing image sensor 115, such as a CCD or a CMOS image sensor. The first side-pointing image sensor 115 is mounted on an integrated circuit board 116, which may be rigid or flexible. The integrated circuit board 116 supplies the first side-pointing image sensor 115 with the necessary electrical power, and derives still images and/or video feeds captured by the image sensor 115. The integrated circuit board 116 is connected to a set of electrical cables which are threaded through an electrical channel running through the elongated shaft of the endoscope.

The first side-pointing image sensor 115 has a lens assembly 117 mounted on top of it and providing the necessary optics for receiving images. The lens assembly 117 includes a plurality of lenses, static or movable, which provide a field of view of at least 90 degrees and up to essentially 180 degrees. The lens assembly 117 provides a working distance of about 5 to 100 millimeters, in one embodiment. In another embodiment, the lens assembly 117 provides a working distance of 2 to 5 millimeters. The first side-pointing image sensor 115 and the lens assembly 117 are jointly referred to as a "first side-pointing viewing element".

One or more discrete side illuminators 118 are placed next to the lens assembly 117, for illuminating its field of view. Optionally, discrete front illuminators 118 may be attached to the same integrated circuit board 116 on which the first side-pointing image sensor 115 is mounted.

Thus, in some embodiments, side-pointing viewing element which comprises lens assembly 117 and side-pointing image sensor 115, mounted on integrated circuit board 116, and associated with at least one illuminator 118 forms a first side-pointing optical assembly.

In another configuration, the integrated circuit boards 106 and 116 are configured as a single integrated circuit board on which both the front and the first side-pointing image sensors 105 and 115 are mounted. For this purpose, the integrated circuit board is essentially L-shaped.

In some embodiments, the endoscope tip section 100a includes a second side-pointing image sensor 125, such as a CCD or a CMOS image sensor. Side-pointing image sensor 125 is mounted on an integrated circuit board 126, which may be rigid or flexible. Integrated circuit board 126 supplies the side-pointing image sensor 125 with the necessary electrical power, and derives still images and/or video feeds captured by the image sensor 125. The integrated circuit board 126 is connected to a set of electrical cables which are threaded through an electrical channel running through the elongated shaft of the endoscope.

The side-pointing image sensor 125 has a lens assembly 127 mounted on top of it and providing the necessary optics for receiving images. Lens assembly 127 includes a plurality of lenses, static or movable, which provide a field of view of at least 90 degrees and up to essentially 180 degrees. The lens assembly 127 provides a working distance of about 2 to 5 millimeters, in one embodiment. In another embodiment, the lens assembly 117 provides a working distance of 3 to 40 millimeters. The side-pointing image sensor 125 and the lens assembly 127, are jointly referred to as a "second side-pointing viewing element".

One or more discrete side illuminators 128 are placed next to the lens assembly 127, for illuminating its field of view. Optionally, discrete front illuminators 128 may be attached to the same integrated circuit board 126 on which side-pointing image sensor 125 is mounted.

Thus, in some embodiments, the second side-pointing viewing element which comprises lens assembly 127 and side-pointing image sensor 125, mounted on integrated circuit board 126, and associated with at least one illuminator 128 forms a side-pointing optical assembly.

In another configuration, integrated circuit boards 106, 116 and 126 are configured as a single integrated circuit board on which both front and side-pointing image sensors 105, 115 and 125 are mounted. For this purpose, the integrated circuit board is essentially an inverted upside down "U" shape.

For simplicity of presentation, FIG. 1 only shows the viewing elements, associated components and illuminators (optical assemblies) of the multi focus, multiple viewing element endoscope tip section 100a. It is understood that endoscope tip section 100a may include one or more working channels, to enable insertion of multiple surgical tools simultaneously. Similarly, endoscope tip section 100a may include one or more fluid channels, such as for separately feeding at least one of a front fluid injector, a side fluid injector and/or a pathway fluid injector, as well as for separately providing suction through the pathway fluid injector. Endoscope tip section 100a may include one or more electrical cables threaded through an elongated shaft and/or a bending section for controlling the endoscope's cameras and illuminators.

Figure 2:
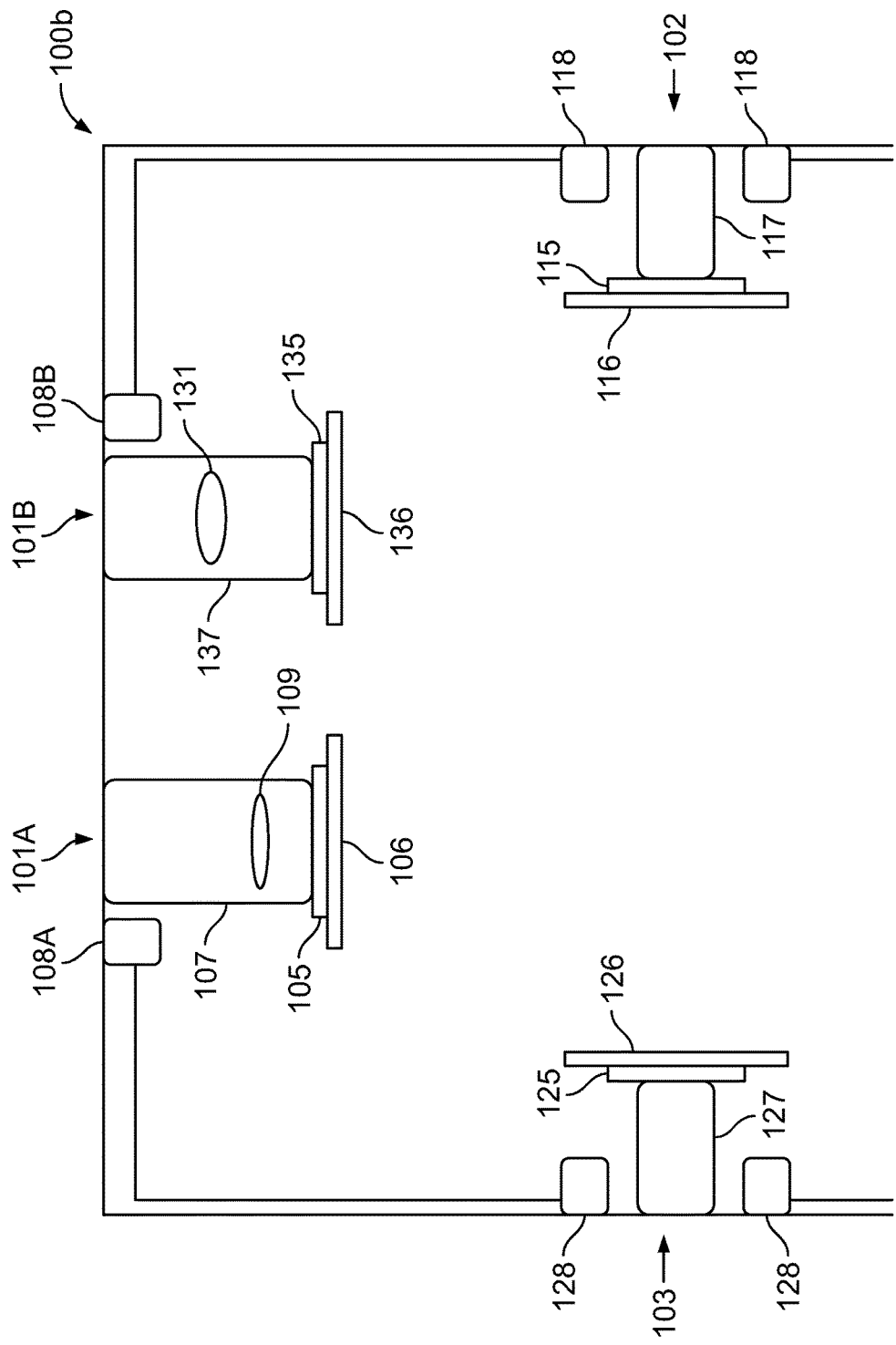
FIG. 2 is a cross-section view of a multi-camera endoscope tip section having a multi-focal front-pointing composite optical assembly, in accordance with an embodiment.

Reference is now made to FIG. 2, which shows a cross section of a multi focal, multi-camera endoscope tip section 100b having two front pointing viewing elements and thus, optical assemblies, according to certain embodiments. Endoscope tip section 100b includes first and second front-pointing optical assemblies, 101A and 101B, also referred to together as a 'composite multi-focal optical assembly' which are positioned at a distal end of an endoscope, such as a colonoscope. The endoscope tip section 100b includes a first side-pointing optical assembly 102 and a second side pointing optical assembly 103. In various embodiments, the first and second side-pointing optical assemblies 102, 103 are positioned such that their optical axes are at a distance ranging between 6 mm and 10 mm from the distal end of the endoscope. The front-pointing optical assemblies 101A, 101B and the first and second side-pointing optical assemblies 102, 103 each have a field of view (FOV) ranging between 150 to 170 degrees, in various embodiments.

Front-pointing optical assembly 101A includes a first front-pointing viewing element having a front-pointing image sensor 105. Front-pointing image sensor 105 has a lens assembly 107 mounted on top of it and providing the necessary optics for receiving images. Lens assembly 107 includes a plurality of lenses, static or movable, which provide a field of view of at least 90 degrees and up to essentially 180 degrees. Lens assembly 107 provides a first working distance of about 5 to 100 millimeters.

Front-pointing image sensor 105 is mounted on a first integrated circuit board 106.

Front-pointing image sensor 105 and lens assembly 107, when coupled to integrated circuit board 106, are jointly referred to as a "first front-pointing optical assembly".

Front-pointing optical assembly 101B includes a second front-pointing viewing element having a front-pointing image sensor 135. Front-pointing image sensor 135 has a lens assembly 137 mounted on top of it and providing the necessary optics for receiving images. Lens assembly 137 includes a plurality of lenses, static or movable, which provide a field of view of at least 90 degrees and up to essentially 180 degrees. Lens assembly 137 provides a second working distance of about 2 to 5 millimeters.

Front-pointing image sensor 135 is mounted on a second integrated circuit board 136.

Front-pointing image sensor 135 and lens assembly 137, when coupled to integrated circuit board 136, are jointly referred to as a "second front-pointing optical assembly".

In accordance with an embodiment, the first front-pointing optical assembly 101A is a default endoscope front-pointing viewing element that includes image sensor 105 and lens assembly 107 having lens 109 providing the first working distance of 5 to 100 millimeters. Lens 109 is used during endoscopic procedures in order to navigate endoscope tip section 100b in patients' colons, for example, and is configured to identify anomalies or objects of interest, such as polyps, from relatively long distance and with relatively low magnification. One or more discrete illuminators 108A are placed next to lens assembly 107, for illuminating its field of view. Optionally, discrete front illuminators 108A are attached to the same integrated circuit board 106 on which the front-pointing image sensor 105 is mounted.

The second front-pointing optical assembly 101B is an increased magnification camera that includes image sensor 135 and lens assembly 137 having lens 131 providing the second working distance of 3 to 6 millimeters. Lens 131 is configured to increase magnification of the identified object of interest. One or more discrete illuminators 108B are placed next to lens assembly 137, for illuminating its field of view. Optionally, discrete front illuminators 108B are attached to the same integrated circuit board 136 on which front-pointing image sensor 135 is mounted.

The endoscope tip section 100b includes, in accordance with certain embodiments, a first side-pointing optical assembly 102 comprising a lens assembly 117 mounted on an image sensor 115 which is in turn mounted on an integrated circuit board 116. The first side-pointing optical assembly 102 also has one or more associated discrete illuminators 118. The endoscope tip section 100 also includes, in various embodiments, a second side-pointing optical assembly 103 comprising a lens assembly 127 mounted on an image sensor 125 which is in turn mounted on an integrated circuit board 126. The second side-pointing optical assembly 103 has one or more associated discrete illuminators 128. According to some embodiments, a focal length of the front-pointing optical assemblies 101A, 101B is on or about the order of 1.1 mm while that of the first and second side-pointing assemblies 102, 103 is on or about the order of 1.0 mm.

Figure 3A:
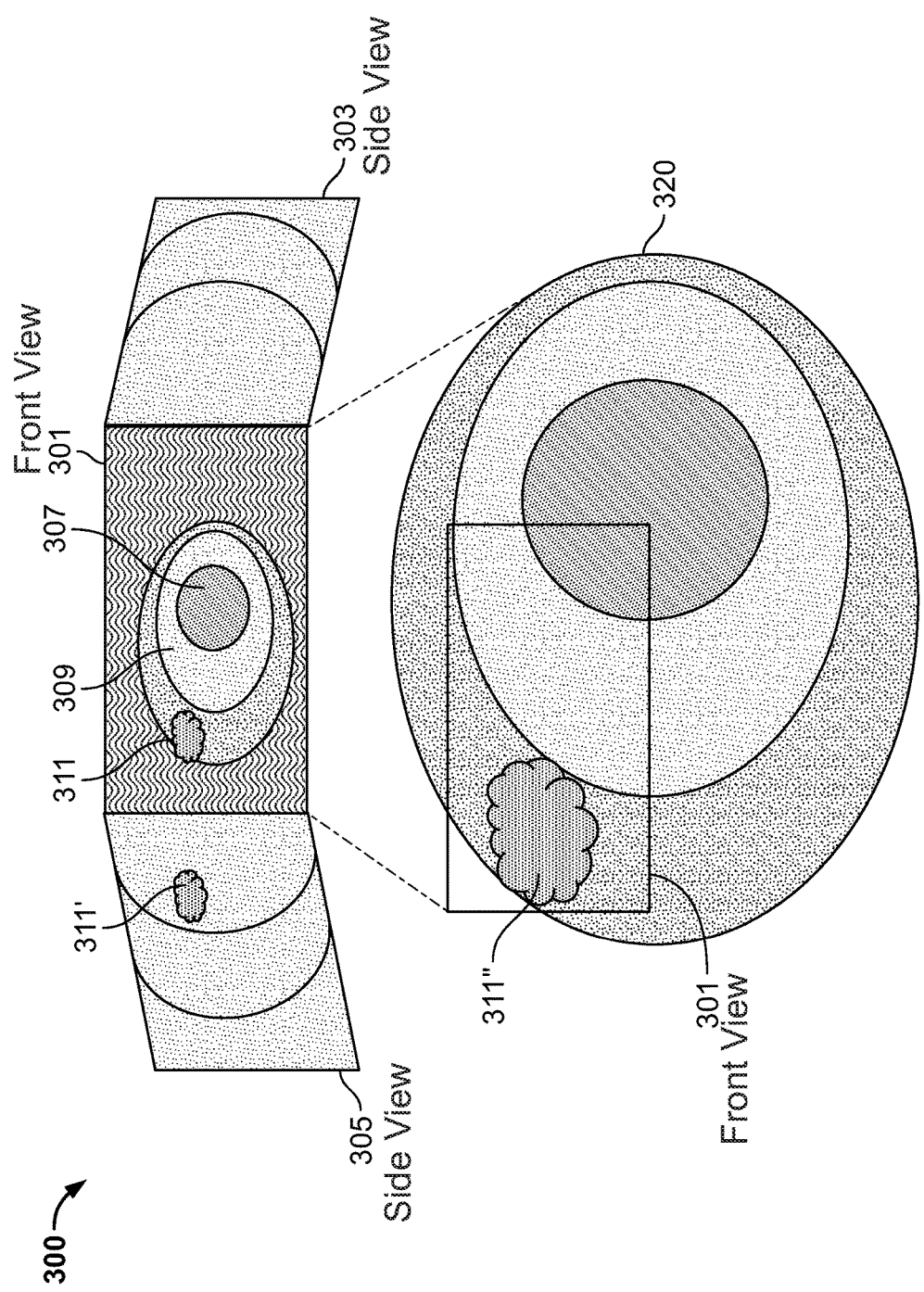
FIG. 3A is a multi-camera display system comprising three screens to display images and/or videos obtained by a multi-camera endoscope tip section.

Reference is now made to FIGS. 1, 2 along with FIGS. 3A through 3C, which illustrate exemplary content displayable on a multi-focal, multi-camera endoscope display system 300, according to certain embodiments. The endoscope display system 300 includes a front view screen 301 used to display images captured by the front-pointing optical assembly 101 of FIG. 1 or by the optical assembly 101A of FIG. 2 (depending upon whether the endoscope tip section 100a or 100b is being used), a first side-pointing screen 303 used to display images captured by the first side pointing optical assembly 102, shown in FIGS. 1, 2, and a second side-pointing screen 305 used to display images captured by the second side-pointing optical assembly 103, shown in FIGS. 1, 2. Thus, it should be understood that if the endoscope tip section 100a of FIG. 1 is used, the front view screen 301 will display the images captured by the front-pointing optical assembly 101 while the side-pointing screens 303, 305 will respectively display the images captured by the first and second side-pointing optical assemblies 102, 103 shown in FIG. 1. Alternately, if the endoscope tip section 100b of FIG. 2 is used, the front view screen 301 will, by default, display the images captured by the front-pointing optical assembly 101A while the side-pointing screens 303, 305 will respectively display the images captured by the first and second side-pointing optical assemblies 102, 103 shown in FIG. 2.

Thus, screens 301, 303 and 305 are configured to display simultaneously the field of views captured by multi-camera endoscope tip section 100a or 100b, shown in FIGS. 1, 2, providing expanded, 330 degrees of field of view, and allowing a clinician to navigate the endoscope tip section through the interrogated regions conveniently, to identify and treat objects of interest or anomalies.

FIG. 3A shows typical front and side view images of a colon 307, colon folds 309 and an object of interest that may be a polyp 311 shown on front view screen 301. Polyp 311 may also be captured by the side-pointing viewing element 102 from a side viewing angle and is shown on side view screen 305 marked as polyp 311'. In operation, an operator advances endoscope tip section 100a (or 100b of FIG. 2) within a body cavity, such as a colon, while viewing images (commonly a video feed) transmitted by the optical assemblies 101, 102 and 103 of FIG. 1 (or optical assemblies 101A, 102 and 103 of FIG. 2). Upon discovery of an object of interest, such as polyp 311, on a wall of colon 307 for example, the operator may further advance the multi-camera endoscope tip section 100a (or 100b of FIG. 2) to the vicinity of the polyp 311. After advancing the endoscope tip section 100a (or 100b of FIG. 2) to an "optimal distance" from the colon (or any body cavity) wall/polyp/any other point of interest, the operator may obtain a magnified object image 320 using the second working distance lens 111 of FIG. 1 (when using the endoscope tip section 100a of FIG. 1) or the second front-pointing optical assembly 101B (when using the endoscope tip section 100b of FIG. 2).

According to some embodiments, the "optimal distance" is determined by the operator, or is determined by a spacer/distance determining member in various embodiments. According to some embodiments, the "optimal distance" is, for example, 2-4 millimeters from the colon (or any body cavity) wall/polyp/any other point of interest. According to the magnified image 311" of the polyp 311, the operator may decide to insert a surgical tool through a working channel of the endoscope to remove, treat and/or extract a sample of the polyp 311 or its entirety for biopsy.

Reference is now made to FIG. 3B, which shows the magnified image 311" on the front view screen 301. Polyp 311 is shown magnified significantly, occupying a larger screen area of the front view screen 301. Magnification of the side view screens 303, 305 is not changed and polyp 311' is still shown on the side view screen 305 with default magnification. However, zooming in and magnifying the polyp 311, by about 30% or more for example, on the front view screen 301, while the side view screen images 303 and 305 are displayed with default magnification, may cause a loss of visual orientation and generally visual fatigue and discomfort to the operator.

Reference is now made to FIG. 3C, which shows a magnified image 311" on the front view screen 301 and disabled, blackened and/or darkened side view screens 303 and 305. Polyp 311 is shown magnified significantly, as image 311", and occupying a large screen area of the front view screen 301 while the two side view screens 303 and 305 are disabled, darkened and/or blackened. Disabling, darkening and/or blackening the side view screens 303 and 305 allows the operator to interrogate the magnified polyp image 311" with no visual disturbances or distractions.

While zooming in and magnifying an image of an object of interest, such as that of the polyp 311, using increased magnification lens 111 of FIG. 1 (when using the endoscope tip section 100a of FIG. 1) or the second front-pointing optical assembly 101B (when using the endoscope tip section 100b of FIG. 2), according to aspects and embodiments of the present specification, a processor is configured to enable any one or a combination of the following: a) disable the side pointing optical assemblies (102 and 103 of FIGS. 1, 2) such as by cutting off or reducing their power supply, while the side pointing illuminators (118, 128—associated with the side pointing optical assemblies 102 and 103 of FIG. 1, 2) continue to stay switched on and the two side pointing screens or monitors (303 and 305) also continue to be switched on, b) switch off or reduce the illumination intensity of the side pointing illuminators (118, 128 of FIGS. 1, 2) associated with the side pointing optical assemblies while the side pointing optical assemblies continue to capture live images and/or video streams and the two side view screens (303 and 305) also continue to be switched on, and/or c) terminate the presentation of the side pointing screens or monitors (303 and 305) obtained from the side pointing optical assemblies on the two side pointing screens (303 and 305) by switching off, darkening or blackening of the two side pointing screens while the side pointing optical assemblies (102, 103 of FIGS. 1, 2) continue to capture live images and/or video streams and the illuminators (118, 128 of FIGS. 1, 2) associated with the side pointing optical assemblies also continue to remain switched on.

Also in one embodiment, the disabling of the side pointing optical assemblies, associated illuminators and/or switching off, blackening or darkening of the two side pointing screens is automatically enabled by the processor when the increased magnification lens 111 of FIG. 1 (when using the endoscope tip section 100a of FIG. 1) or the second front-pointing optical assembly 101B (when using the endoscope tip section 100b of FIG. 2) is enabled for magnified viewing of the object of interest. In another embodiment, the operator manually enables, such as by manipulating one or more switches on the handle of the endoscope, any one or combination of disabling of the side pointing optical assemblies, associated illuminators and/or switching off, blackening or darkening of the two side pointing screens, when the increased magnification lens 111 of FIG. 1 (when using the endoscope tip section 100a of FIG. 1) or the second front-pointing optical assembly 101B (when using the endoscope tip section 100b of FIG. 2) is enabled for magnified viewing of the object of interest.

With reference to FIG. 2, according to aspects and embodiments of the present specification, the processor is configured to turn on, for zooming in, front pointing optical assembly 101B, to turn off front pointing optical assembly 101A, to turn off the illumination associated with the front pointing optical assembly 101A (that is, turning off the one or more illuminators 108A for example) and to display the magnified image captured by the front pointing optical assembly 101B replacing the image captured by the front pointing optical assembly 101A on the front view screen 301. The processor is further configured to enable any one or a combination of the following: a) turn off, for zooming in, the side pointing optical assemblies 102 and 103 while the associated illuminators 118, 128 stay switched on and the side pointing screens 303, 305 also continue to be switched on, b) switch off the side pointing illuminators 118 and 128 associated with the side pointing optical assemblies 102 and 103 while the side pointing optical assemblies 102, 103 continue to capture live image and/or video streams and the side pointing screens 303, 305 also continue to be switched on and/or c) switch off, darken or blacken the presentation of the side pointing screens 303 and 305 while the side pointing optical assemblies 102, 103 continue to capture live image and/or video streams and the side pointing illuminators 118, 128 also continue to stay switched on.

Also in one embodiment, the disabling of the side pointing optical assemblies, associated illuminators and/or switching off, blackening or darkening of the two side pointing screens is automatically enabled by the processor when using the second front-pointing optical assembly 101B is enabled for magnified viewing of the object of interest. In another embodiment, the operator manually enables, such as by manipulating one or more switches on the handle of the endoscope, any one or combination of disabling of the side pointing optical assemblies, associated illuminators and/or switching off, blackening or darkening of the two side pointing screens, when the second front-pointing optical assembly 101B is enabled for magnified viewing of the object of interest.

Figure 4:
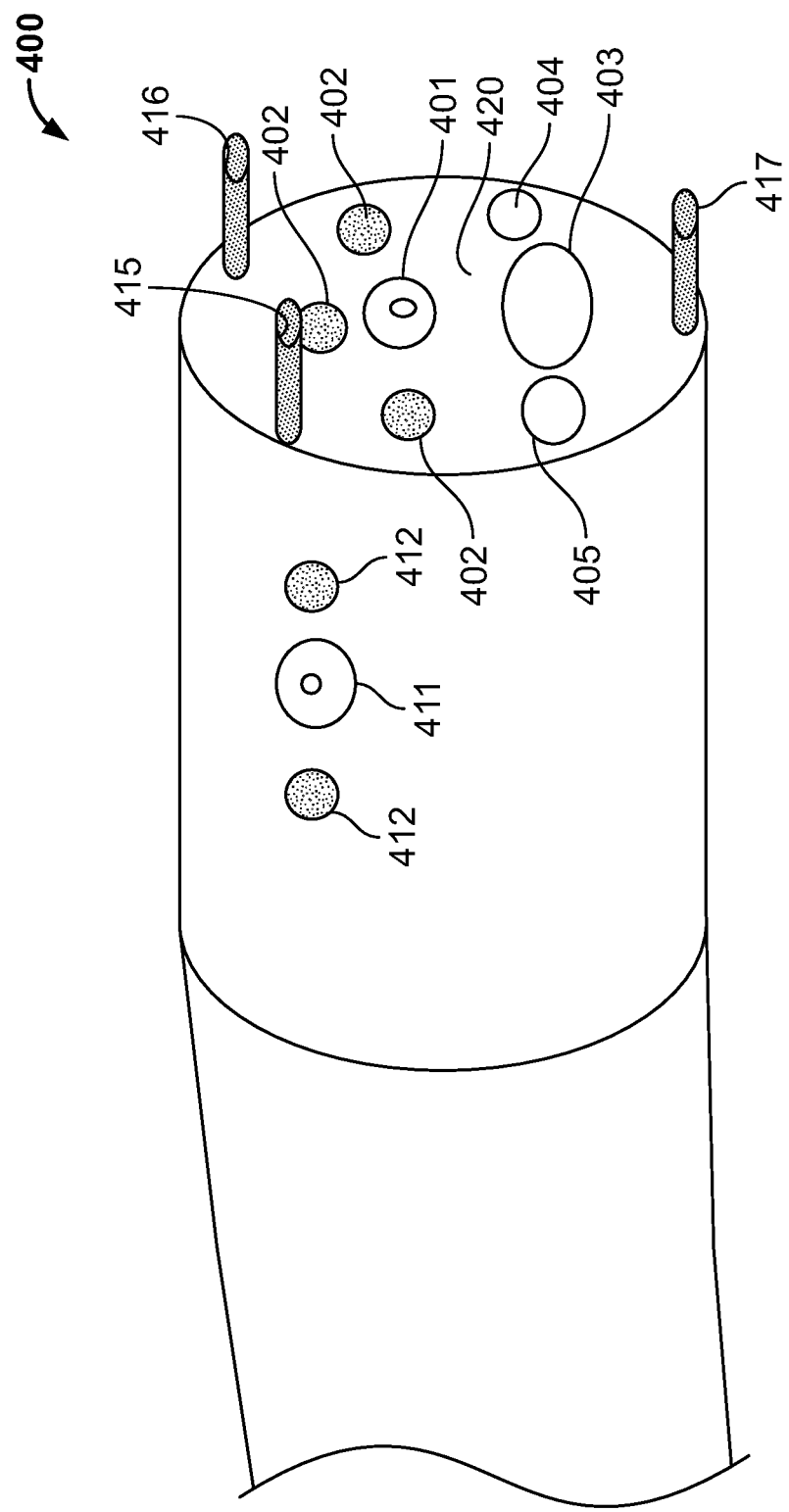
FIG. 4 is the endoscope tip section of FIGS. 1A, 1B with a plurality of distance determining members in deployed configuration.

Reference is now made to FIG. 4, which shows a perspective view of a multi-focal, multi-camera endoscope tip section 400 comprising one or more distance determining members or spacers. The endoscope tip section 400 includes a front-pointing optical assembly 401, associated with one or more front-pointing illuminators 402, a working channel 403, a fluid injection channel 404, a fluid injection channel 405 for cleaning the optical assembly 401 and illuminators 402, a side-pointing optical assembly 411 which is associated with one or more side-pointing illuminators 412.

In accordance with an embodiment, the endoscope tip section 400 includes one or more, preferably three or more, distance determining members or spacers 415, 416 and 417 configured to contact an inner wall of a body cavity, such as that of a colon for example, and fix or maintain the distance between the optical assembly 401 and the inner wall of the colon. In various embodiments, the three or more distance determining members 415, 416 and 417 are one or more spacers, protuberances, protrusions or projections that are fixedly mounted on the distal end 420 of the tip section 400 or retractably pulled out of the endoscope tip section 400, when needed.

In accordance with various embodiments, a protruding length of the three or more distance determining members 415, 416 and 417, beyond the distal end 420, approximately matches the second working distance of the magnifying second lens 111 of FIG. 1 or that of the second front-pointing optical assembly 101B of FIG. 2. Thus, in various embodiments, the protruding length of the three or more distance determining members or spacers 415, 416 and 417 ranges from 3 to 7 mm. In some embodiments, the protruding length of the three or more distance determining members or spacers 415, 416 and 417 ranges between 1.5 to 7 mm. In one embodiment, the protruding length of the three or more distance determining members or spacers 415, 416 and 417 is limited to 2 mm to ensure that the field of view of the optical assembly 401 is not distorted by the spacers 415, 416 and 417. In certain embodiments where the distance determining members 415, 416 and 417 can be retractably pulled out of the distal end 420, the protruding length of the distance determining members 415, 416 and 417 can be dynamically varied in order to match the second working distance. In various embodiments, the three or more distance determining members 415, 416, 417 are spaced from each other such that a distance between any two of the distance determining members ranges between 8 to 10 mm.

According to some embodiments, the distance determining members are configured to provide distance determination or spacing of approximately 4 mm. According to some embodiments, the distance determining members are configured to provide distance determination of more than 5 mm. According to other embodiments, the distance determining members are configured to controllably provide distance determination for more than one distance ranging between 3 mm and 12 mm. According to still other embodiments, the distance determining members are configured to controllably provide distance determining for more than one distance ranging between 4 mm and 6 mm. According to various embodiments, the distance determining members are configured to provide dynamic distance determination according to the working distance.

Figure 5:
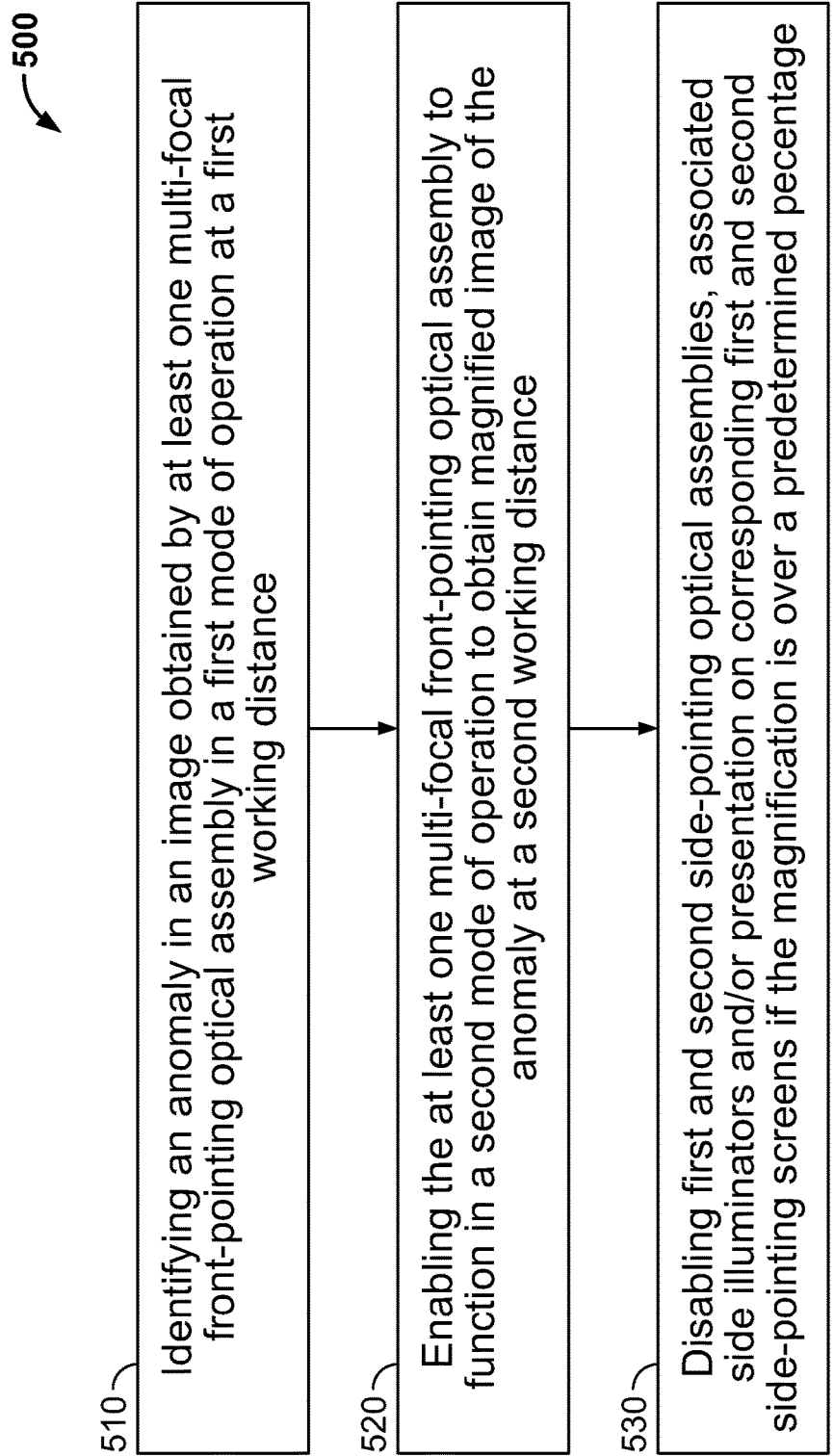
FIG. 5 is a flowchart illustrating a plurality of exemplary steps of a method of obtaining a magnified view of an area or object of interest within a body cavity, such as a colon, using a multi-focal front pointing optical assembly of a multi focal, multi-camera endoscope tip section.

FIG. 5 is a flowchart illustrating a plurality of exemplary steps of a method 500 of obtaining a magnified view of an area or object of interest within a body cavity, such as a colon, using a multi focal, multi-camera endoscope tip section of an endoscope, such as a colonoscope. A processor, associated with the endoscope, is configured to implement the method 500. Referring now to FIGS. 1, 2 and 5, at step 510 a multi focal, multi-camera endoscope tip section, such as the tip section 100a or 100b, is navigated into a patient's colon in a first mode of operation of at least one multi-focal front-pointing optical assembly (that is, the front-pointing optical assembly 101 of the tip section 100a or the first front-pointing optical assembly 101A of the tip section 100b) to identify an anomaly, area or object of interest—such as a polyp. During the first mode of operation the at least one multi-focal front-pointing optical assembly obtains images and/or videos of the colon at a first working distance. The at least one multi-focal front-pointing optical assembly is enabled to function at the first working distance using a first lens 109 or a first front-pointing optical assembly 101A (while the second front-pointing optical assembly 101B is disabled) depending upon whether the endoscope tip section 100a or 100b is being used. In one embodiment, the endoscope tip section is operated in the first mode, by default.

The images and/or videos obtained from the at least one multi-focal front-pointing optical assembly, in the first mode of operation, are displayed on a front view screen along with an identified anomaly, while the images and/or videos obtained from a first and a second side-pointing optical assemblies are displayed respectively on corresponding first and second side-pointing screens. It should be appreciated that the identified anomaly visible on the front view screen, as captured by the at least one multi-focal front-pointing optical assembly, may also be simultaneously displayed on at least one of the first or second side-pointing screens as captured in an overlapping field of view of at least one of the first or second side-pointing optical assemblies. In various embodiments, during the first mode of operation a magnification of 100×-6× of the captured image of the anomaly is enabled for the first working distance.

At step 520, the processor enables the at least one multi-focal front-pointing optical assembly to function in a second mode of operation in order to obtain and display a magnified image, comprising the identified anomaly, on the front view screen. During the second mode of operation the at least one multi-focal front-pointing optical assembly obtains the magnified image at a second working distance. The at least one multi-focal front-pointing optical assembly is enabled to function at the second working distance by switching to using a second lens 111 or by activating a second front-pointing optical assembly 101B (while simultaneously disabling the first front-pointing optical assembly 101A) depending upon whether the endoscope tip section 100a or 100b is being used. In various embodiments, during the second mode of operation the enabled magnification of the captured image of the anomaly ranges between 250×-100× for the second working distance.

In accordance with an embodiment, a distance between the at least one multi-focal front-pointing optical assembly and the identified anomaly or object of interest is maintained by pulling or deploying one or more distance determining members, such as the members 415, 416 and 417 of FIG. 4, out of a distal end of the endoscope tip section and advancing the tip section until the one or more distance determining members contact the anomaly or the inner wall of the colon thereby maintaining the distance to approximately the second working distance. In this embodiment, a length of the distance determining members can be varied by retracting or deploying them partially or fully. In other embodiments, the distance determining members are affixed to the distal end and are of a fixed length approximately matching the second working distance. Operationally, this structure has the benefit of ensuring a minimum distance is kept between the endoscope camera(s) and tissue being observed.

At step 530, when the magnification of the magnified image on the front view screen is over a predetermined percentage, the processor enables any one or a combination of the following: a) turns off or disables the first and second side-pointing optical assemblies while the illuminators associated with the first and second side-pointing optical assemblies stay switched on and the first and second side pointing screens also continue to be switched on, b) switch off the side illuminators associated with the first and second side-pointing optical assemblies while the first and second side-pointing optical assemblies continue to capture and generate live images and/or video streams and the first and second side pointing screens also continue to be switched on, and/or c) switch off, blacken or darken presentation of the images and/or videos on the first and second side-pointing screens while the first and second side-pointing optical assemblies continue to capture and generate live images and/or video streams and the illuminators associated with the first and second side-pointing optical assemblies also continue to stay switched on. In some embodiments, the predetermined magnification percentage is about 30% or more.

If required, a surgical tool may be inserted through a working channel of the endoscope in order to remove, treat and/or extract a sample of the anomaly or object of interest or its entirety for biopsy, while viewing the magnified image.

In accordance with an embodiment, actuating a button or switch on a handle of the endoscope prompts the processor to switch the endoscope tip section from the first mode of operation to the second mode of operation.

Figure 6A:
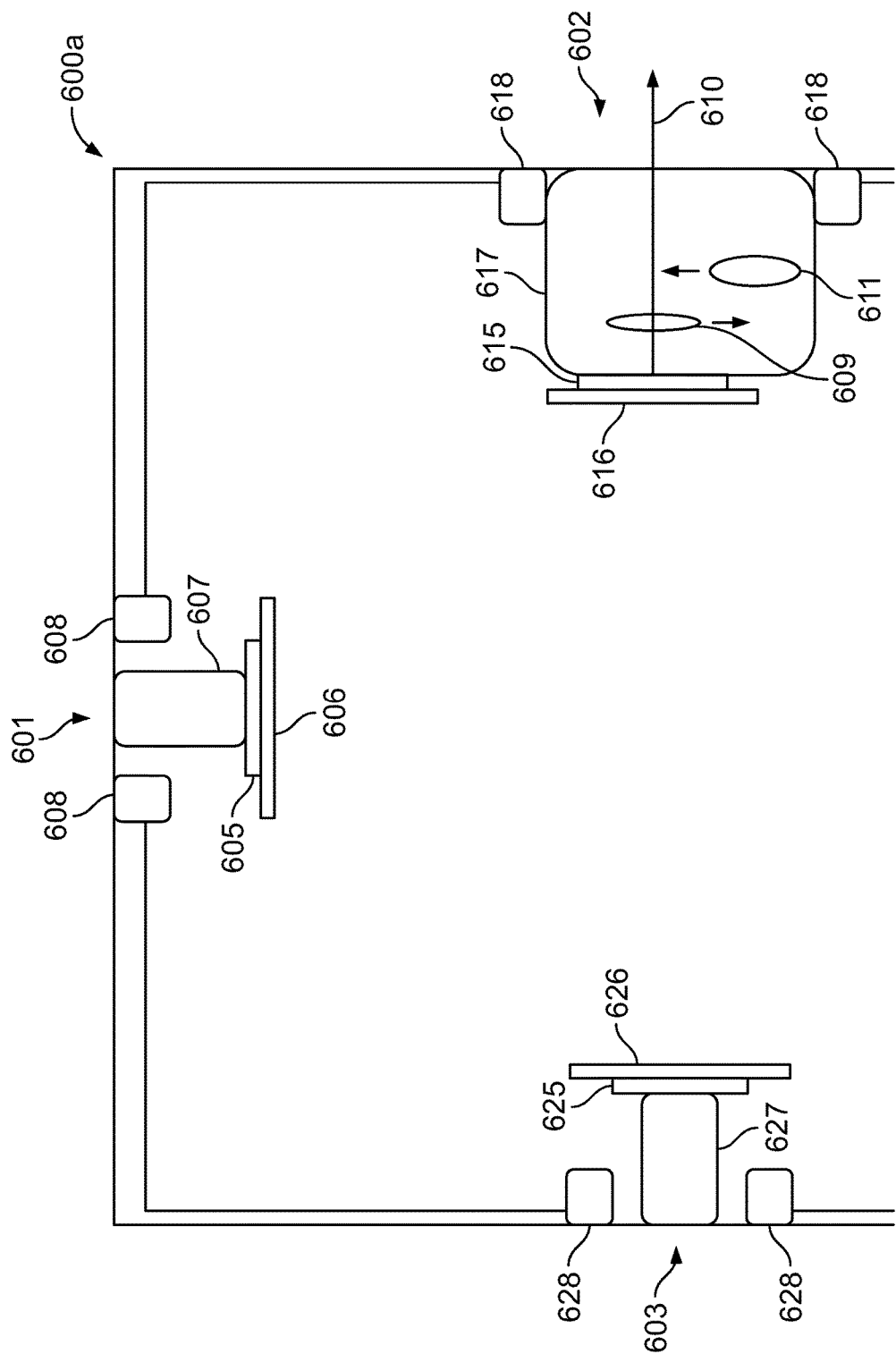
FIG. 6A is a cross-section view of a multi-camera endoscope tip section having a multi-focal first side-pointing optical assembly, in accordance with an embodiment.

Reference is now made to FIG. 6A, which shows a cross-section of a multi-focal, multi-camera endoscope tip section, according to certain embodiments. Endoscope tip section 600a includes a front-pointing optical assembly 601 that is positioned at a distal end of an endoscope, such as a colonoscope. The front-pointing optical assembly 601 typically has a wide field of view of 170 degrees. The endoscope tip section 600a includes a first multi-focal side-pointing optical assembly 602 and a second side-pointing optical assembly 603. The two side-pointing optical assemblies 602 and 603 and front-pointing optical assembly 601 are configured to provide an expanded field of view of about 330 degrees. In various embodiments, the first and second side-pointing optical assemblies 602, 603 are positioned such that their optical axes are at a distance ranging between 6 mm and 10 mm from the distal end of the endoscope. The front-pointing, first and second side-pointing optical assemblies 601, 602, 603 each have a field of view (FOV) ranging between 150 to 170 degrees, in various embodiments.

While the front-pointing optical assembly 601 is able to detect objects of interest, such as polyps, visible in the front field of view, side-pointing optical assemblies 602 and 603 are further able to detect objects of interest, which may be hidden from the front-pointing optical assembly 601, for example within the inner sides of the folds of a colon. According to some embodiments, a focal length of the front-pointing optical assembly 601 is on the order of 1.1 mm while that of the first and second side-pointing assemblies 602, 603 is on the order of 1.0 mm.

The front-pointing optical assembly 601 includes a front-pointing viewing element or camera having a front-pointing image sensor 605 such as Charge Coupled Device (CCD) or a Complementary Metal Oxide Semiconductor (CMOS) image sensor. The front-pointing image sensor 605 has a lens assembly 607 mounted on top of it to provide the necessary optics for receiving images. The lens assembly 607 includes a plurality of lenses, static or movable, which provide a field of view of at least 90 degrees and up to essentially 180 degrees.

The front-pointing image sensor 605 is mounted on an integrated circuit board 106, which may be rigid or flexible. The integrated circuit board 606 supplies the front-pointing image sensor 605 with the necessary electrical power, and derives still images and/or video feeds captured by the image sensor 605. The integrated circuit board 606 is connected to a set of electrical cables which are threaded through an electrical channel running through an elongated shaft of the endoscope.

One or more discrete front illuminators 608 are placed next to the lens assembly 607, for illuminating its field of view. Optionally, discrete front illuminators 608 may be attached to the same integrated circuit board 606 on which the front-pointing image sensor 605 is mounted. Thus, in some embodiments, the front-pointing optical assembly 601 includes at least a front pointing-viewing element which comprises lens assembly 107 and front-pointing image sensor 105, mounted on integrated circuit board 106, and associated with at least one illuminator 608.

In one embodiment, the illuminators are optionally discrete illuminators and include a light-emitting diode (LED). Thus, light is provided by light emitting diodes (LED) that illuminates the fields of view. According to some embodiments, white light LEDs are used. According to other embodiments, other colors of LEDs or any combination of LEDs may be used, including but not limited to red, green, blue, infrared, near infrared and ultraviolet or any other LED.

In some embodiments, light may be generated internally within the endoscope tip section 600a, or generated remotely and transferred, for example, by a fiber optic. In some embodiments, two or more illuminators may be employed, wherein at least one may generate the light internally, and at least one may provide remotely generated light.

In accordance with various embodiments, the endoscope tip section 600a includes a first side-pointing image sensor 615, such as CCD or a CMOS image sensor. The first side-pointing image sensor 615 is mounted on an integrated circuit board 616, which may be rigid or flexible. The integrated circuit board 616 supplies the first side-pointing image sensor 615 with the necessary electrical power, and derives still images and/or video feeds captured by the image sensor 615. The integrated circuit board 616 is connected to a set of electrical cables which are threaded through an electrical channel running through the elongated shaft of the endoscope.

The first side-pointing image sensor 615 has a lens assembly 617 mounted on top of it for providing the necessary optics for receiving images. The lens assembly 617 includes a plurality of lenses, static or movable, which provide a field of view of at least 90 degrees and up to essentially 180 degrees. The lens assembly 617 provides a working distance of about 2 to 40 millimeters, in one embodiment. In another embodiment, the lens assembly 617 provides a working distance of 2 to 6 millimeters. The first side-pointing image sensor 615 and the lens assembly 617, are jointly referred to as a "first side-pointing viewing element".

One or more discrete side illuminators 618 are placed next to the lens assembly 617, for illuminating its field of view. Optionally, discrete front illuminators 618 may be attached to the same integrated circuit board 616 on which the first side-pointing image sensor 615 is mounted.

Thus, in some embodiments, side-pointing viewing element which comprises lens assembly 617 and first side-pointing image sensor 615, mounted on integrated circuit board 616, and associated with at least one illuminator 618 forms a first side-pointing optical assembly.

In another configuration, the integrated circuit boards 606 and 616 may be a single integrated circuit board on which both the front and the first side-pointing image sensors 605 and 615 may be mounted. For this purpose, the integrated circuit board may be essentially L-shaped.

According to some embodiments of the present specification, the lens assembly 617 includes two lenses 609 and 611 that are switched dynamically by the processor in order to shift from a first working distance (associated with the first lens 609) to a second working distance (associated with the second lens 611) to increase image magnification of an anomaly or object of interest, such as, for example, a polyp, captured by the first multi-focal side-pointing optical assembly 602 and associated components.

According to aspects and embodiments of the present specification, shifting from the first working distance to the second working distance allows for increased magnification and an improved image that can be generated by the image sensor 615. Shifting to the second working distance allows using the lens 611 with improved modulation transfer function (MTF) and aberration qualities adapted to a shorter depth of field (DOF) compared to the longer DOF of the first regular lens 609. For example, in one embodiment, the lens assembly 617 provides a first working distance of about 20 millimeters provided by the lens 609 and a second working distance of about 5 millimeters provided by the lens 611. Alternatively, in another embodiment, the lens assembly 617 provides a first working distance of about 10 millimeters provided by the lens 609 and a second working distance of about 2 millimeters provided by the lens 611. It should be appreciated that the lens assembly 617 may provide other lenses with other working distances, typically in the range of 2 to 40 millimeters, and such lenses are within the scope of the present specification.

In accordance with an aspect of the present specification, the lens assembly 617 includes one or more actuation elements configured to control optical elements included in the lens assembly 617. The one or more actuation elements comprise a piezoelectric element, an electric engine, solenoid, a Nitinol engine or any combination thereof. In a preferred embodiment, the actuation elements comprise at least one pneumatic engine. The optical elements comprise lenses (such as lenses 609, 611), mirrors, diffraction elements or any combination thereof.

In various embodiments, the actuation elements are triggered by the processor to push, move or pull the lens 609 out of the optical path 610 and push, move or pull the lens 611 onto the optical path 610 such that the optical path that connects the line of sight from the image sensor 615 to an anomaly or object of interest passes through the first lens 609 or the second lens 611. In some embodiments, the endoscope tip section 600a includes a second side-pointing image sensor 625, such as a CCD or a CMOS image sensor. The second side-pointing image sensor 625 is mounted on an integrated circuit board 626, which may be rigid or flexible. The integrated circuit board 626 supplies the second side-pointing image sensor 625 with the necessary electrical power, and derives still images and/or video feeds captured by the image sensor 625. The integrated circuit board 626 is connected to a set of electrical cables which are threaded through an electrical channel running through the elongated shaft of the endoscope.

The second side-pointing image sensor 625 has a lens assembly 627 mounted on top of it for providing the necessary optics for receiving images. The lens assembly 627 includes a plurality of lenses, static or movable, which provide a field of view of at least 90 degrees and up to essentially 180 degrees. The lens assembly 627 provides a working distance of about 2 to 6 millimeters, in one embodiment. In another embodiment, the lens assembly 627 provides a working distance of 2 to 40 millimeters. The second side-pointing image sensor 625 and the lens assembly 627 are jointly referred to as a "second side-pointing viewing element".

One or more discrete side illuminators 628 are placed next to the lens assembly 627, for illuminating its field of view. Optionally, the discrete front illuminators 628 may be attached to the same integrated circuit board 626 on which the side-pointing image sensor 625 is mounted.

Thus, in some embodiments, the second side pointing-viewing element which comprises lens assembly 627 and side-pointing image sensor 625, mounted on integrated circuit board 626, and associated with at least one illuminator 628 forms a second side-pointing optical assembly.

In another configuration, the integrated circuit boards 606, 616 and 626 are configured as a single integrated circuit board on which both front and side-pointing image sensors 605, 615 and 625 are mounted. For this purpose, the integrated circuit board is essentially an inverted upside down U-shape.

In certain embodiments, the lens assembly 627 may also be a multi-focal (dual focus, for example) lens assembly similar to the lens assembly 617 described hereinabove that includes two lenses (such as the first lens 609 and the second lens 611) that may also be switched dynamically by the processor in order to shift from a first working distance to a second working distance to increase magnification of an image of an object of interest captured by the second side-pointing optical assembly 603.

Optionally and additionally, one or more lens assemblies, described herein above, may further include an autofocus zoom system, an optical zoom system and/or a digital zoom system.

For simplicity of presentation, FIG. 6A only shows the viewing elements, associated components, and illuminators (together, optical assemblies) of the multi-focal, multi viewing element endoscope tip section 600a. It is understood that endoscope tip section 600a may include one or more working channels that enable the insertion of multiple surgical tools simultaneously. Similarly, endoscope tip section 600a may include one or more fluid channels, such as for separately feeding at least one of a front fluid injector, a side fluid injector and/or a pathway fluid injector, as well as for separately providing suction through the pathway fluid injector. The endoscope tip section 600a may also include one or more electrical cables threaded through an elongated shaft and/or a bending section for controlling the endoscope's cameras and illuminators.

Figure 6B:
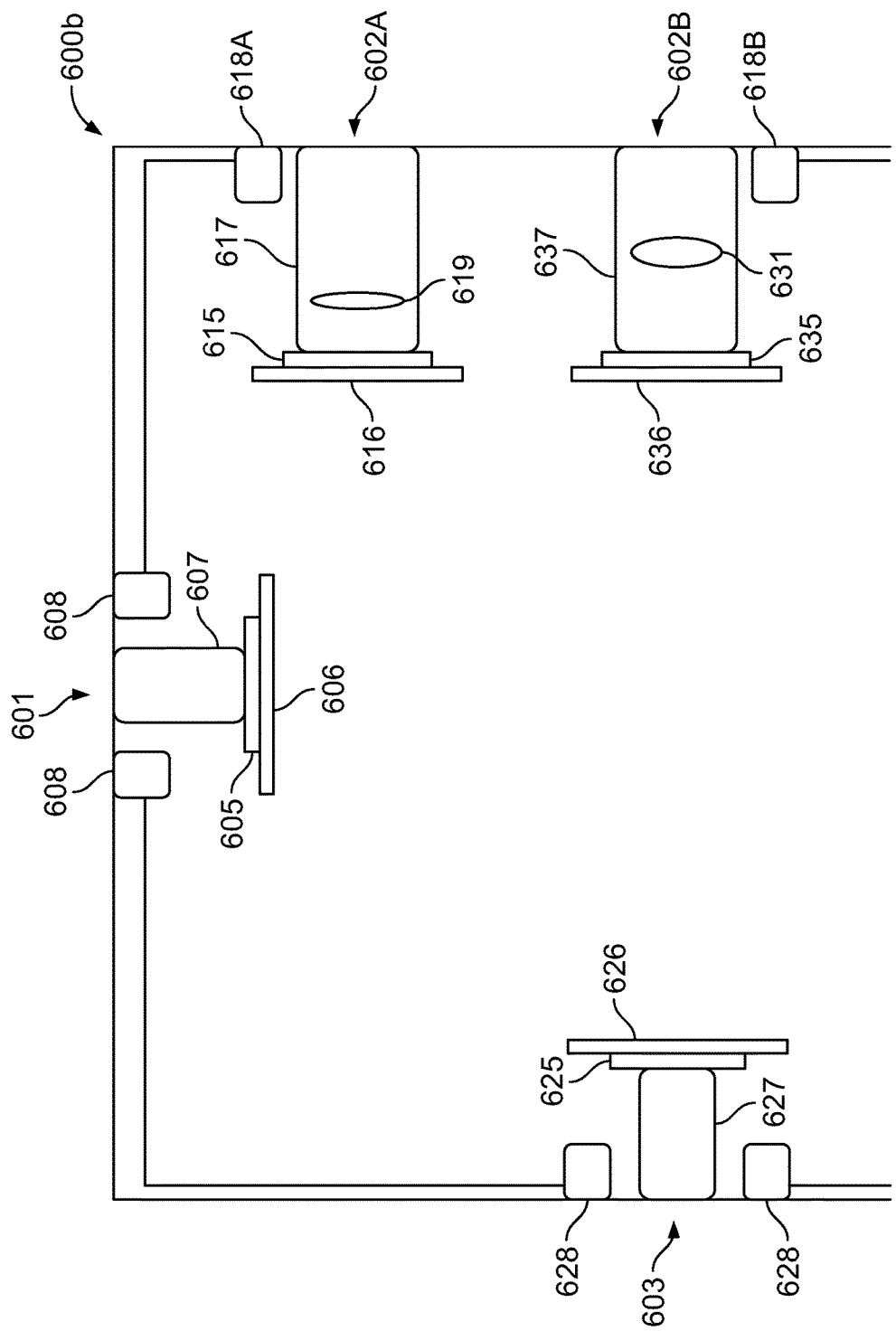
FIG. 6B is a cross-section view of a multi-camera endoscope tip section having a multi-focal first side-pointing composite optical assembly, in accordance with an embodiment.

Reference is now made to FIG. 6B, which shows a cross section of multi-focal, multi-camera endoscope tip section 600b comprising two first side-pointing viewing elements, and thus optical assemblies, according to certain embodiments. The endoscope tip section 600b includes two first side-pointing optical assemblies 602A and 602B, together referred to as a 'composite multi-focal optical assembly', having their field of views directed towards a first side of a distal end of an endoscope, such as a colonoscope. In some embodiments, the endoscope tip section 600b may also include an additional side-pointing optical assembly 603 pointing at an opposing second side relative to the first side.

The first side-pointing first viewing element 602A includes a side-pointing image sensor 615 having a lens assembly 617 mounted on top of it for providing the necessary optics for receiving images. The side-pointing image sensor 615 is mounted on an integrated circuit board 616. The lens assembly 617 includes a plurality of lenses, static or movable, which provide a field of view of at least 90 degrees and up to essentially 180 degrees. The lens assembly 617 provides a working distance of about of about 4 to 40 millimeters, in one embodiment. In another embodiment, the lens assembly 617 provides a working distance of 2 to 5 millimeters. The side-pointing image sensor 615 and the lens assembly 617 when coupled to the integrated circuit board 616 and associated with at least one illuminator 618A, are jointly referred to as a "first side-pointing first optical assembly".

The first side-pointing second viewing element 602B includes a side-pointing image sensor 635 having a lens assembly 637 mounted on top of it and providing the necessary optics for receiving images. The side-pointing image sensor 635 is mounted on an integrated circuit board 636. The lens assembly 637 includes a plurality of lenses, static or movable, which provide a field of view of at least 90 degrees and up to essentially 180 degrees. The lens assembly 637 provides a working distance of about 2 to 5 millimeters, in one embodiment. In another embodiment, the lens assembly 637 provides a working distance of 3 to 6 millimeters. The side-pointing image sensor 635 and the lens assembly 637, when coupled to the integrated circuit board 636 and associated with at least one illuminator 618B, are jointly referred to as a "first side-pointing second optical assembly".

In accordance with an embodiment the first side-pointing first viewing element 602A is a default viewing element for the first side that includes the image sensor 615 and the lens assembly 617 having a lens 619 providing a first working distance of 2 to 40 millimeters. The lens 619 is used during endoscopic procedures in order to navigate the endoscope tip section 600b in patients' colons, for example, and is configured to identify objects of interest from relatively long distance and with relatively low magnification. One or more discrete illuminators 618A are placed next to the lens assembly 617, for illuminating its field of view. Optionally, discrete side illuminators 618A are attached to the same integrated circuit board 616 on which the side-pointing image sensor 615 is mounted.

The first side-pointing second viewing element 602B is an increased magnification camera that includes image sensor 635 and lens assembly 637 having lens 631 for providing a second working distance of 2 to 6 millimeters. The lens 631 is configured to increase magnification of the identified object of interest. One or more discrete illuminators 618B are placed next to the lens assembly 637, for illuminating its field of view. Optionally, discrete side illuminators 618B are attached to the same integrated circuit board 636 on which the side-pointing image sensor 635 is mounted.

The endoscope tip section 600b includes, in accordance with certain embodiments, a front-pointing optical assembly 601 comprising a lens assembly 607 mounted on an image sensor 605 which is in turn mounted on an integrated circuit board 606. The front-pointing optical assembly 601 also has one or more associated discrete illuminators 608. The endoscope tip section 600b also includes, in various embodiments, a second side-pointing optical assembly 603 comprising a lens assembly 627 mounted on an image sensor 625 which is in turn mounted on an integrated circuit board 626. The second side-pointing optical assembly 603 has one or more associated discrete illuminators 628. In various embodiments, the first and second side-pointing optical assemblies 602A, 603 are positioned such that their optical axes are at a distance ranging between 6 mm and 10 mm from the distal end of the endoscope. The first side-pointing optical assemblies 602A, 602B and the front-pointing and second side-pointing optical assemblies 601, 603 each have a field of view (FOV) ranging between 150 to 170 degrees, in various embodiments.

Optionally, in additional embodiments, the optical assembly 603 may also include two second side-pointing optical assemblies similar to the first side-pointing first optical assembly 602A and the first side-pointing second optical assembly 602B described herein above. According to some embodiments, a focal length of the front-pointing optical assembly 601 is on the order of 1.1 mm while that of the first and second side-pointing assemblies 602 (602A, 602B), 603 is on the order of 1.0 mm.

Figure 7A:
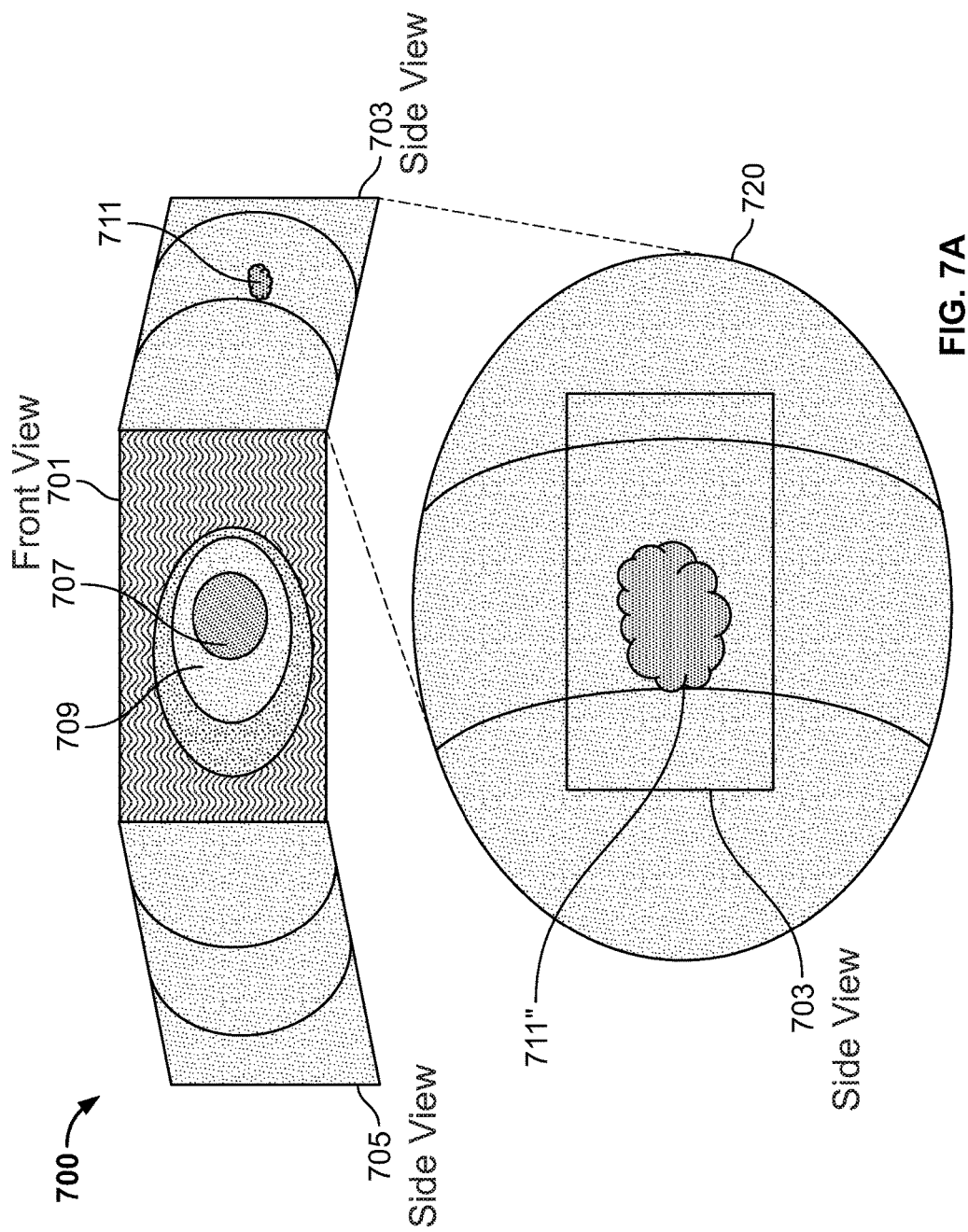
FIG. 7A is a multi-camera display system comprising three screens to display images and/or videos obtained by a multi-camera endoscope tip section.

Reference is now made to FIGS. 6A, 6B along with FIGS. 7A through 7C, which illustrate exemplary content displayable on a multi-focal, multi-camera endoscope display system 700, according to certain embodiments. The endoscope display system 700 comprises a front view screen 701 used to display images captured by the front-pointing optical assembly 601 shown in FIGS. 6A, 6B, a first side-view screen 703 used to display images captured by the first side-pointing optical assembly 602 of FIG. 6A or the first side-pointing first optical assembly 602A of FIG. 6B (depending upon whether the endoscope tip section 600a or 600b is being used), and a second side-view screen 705 used to display images captured by the second side-pointing optical assembly 703, shown in FIGS. 6A, 6B. Thus, it should be understood that if the endoscope tip section 600a of FIG. 6A is used, the front view screen 701 will display the images captured by the front-pointing optical assembly 601 while the side-pointing screens 703, 705 will respectively display the images captured by the first and second side-pointing optical assemblies 602, 603 shown in FIG. 6A. Alternately, if the endoscope tip section 600b of FIG. 6B is used, the front view screen 701 will display the images captured by the front-pointing optical assembly 601 while the side-pointing screens 703, 705 will respectively display the images captured by the first side-pointing first optical assembly 602A, by default, and the second side-pointing optical assemblies 603 shown in FIG. 6B.

Thus, the screens 701, 703 and 705 are configured to simultaneously display the field of views captured by the multi-camera endoscope tip section 600a or 600b, shown in FIGS. 6A, 6B, providing an expanded, 330 degrees field of view, and allowing a clinician to navigate the endoscope tip section through the interrogated regions conveniently, to identify and treat objects of interest or anomalies.

FIG. 7A, shows typical front and side view images of a colon 707, colon folds 709 and an object of interest, such as a polyp 711, captured by the first side-pointing optical assembly 602 or the first side-pointing first optical assembly 602A (depending upon whether the endoscope tip section 600a or 600b is being used), and which is shown on the first side view screen 703. An exploded view of the first side view screen 703, displaying a magnified image 720 is shown comprising a magnified image of the polyp 311 and marked therein as 711".

During an endoscopic procedure, when the endoscope tip section 600a or 600b is used within a body cavity such as a colon, the clinician or operator advances the endoscope tip section 600a (or 600b) while viewing images (commonly a video feed) transmitted by the optical assemblies 601, 602 and 603 shown in FIG. 6A (or the optical assemblies 601, 602A and 603 of FIG. 6B). Upon identification or discovery of the polyp 711, on the wall of the colon, the operator may move or advance the endoscope tip section 600a (or the endoscope tip section 600b) to the vicinity of the polyp 711, and may magnify the polyp image using the first side-pointing optical assembly 602 with the second working distance lens 611, shown in FIG. 6A, in accordance with an embodiment. In another embodiment, the operator may magnify the polyp image using the first side-pointing second optical assembly 602B comprising the second working distance lens 631, shown in FIG. 6B. Depending upon the status of the polyp 711 as represented by the magnified image 711", the operator may decide to insert a surgical tool through a working channel of the endoscope to remove, treat and/or extract a sample of the polyp 711 or its entirety for biopsy.

Reference is now made to FIG. 7B, which shows the magnified image 311" on the side view screen 703. The polyp 311 is shown magnified significantly occupying a large part of the side view screen 703. However, the images of the colon 707 and the colon folds 709 are shown with default magnification on the front view screen 701, for example. However, zooming in and magnifying the polyp 311, by about 30% or more, for example, on the first side view screen 703, while the images on the front view screen 701 and the second side view screen 705 are displayed with a default magnification, may cause a loss of visual orientation and generally visual fatigue and discomfort, which may endanger successful interrogation, treatment and/or removal of the polyp by the operator.

Reference is now made to FIG. 7C, which shows a magnified image on the first side view screen 703 and darkened, blackened or disabled front view screen 701 and second side view screen 705. The polyp 311 is shown magnified significantly and occupying a large part of the first side view screen 703 while the other two screens 701 and 705 are disabled, blackened and/or darkened. Disabling, blackening and/or darkening the front view screen 701 and the second side view screen 705 allow the operator to interrogate the magnified polyp image 311" with no visual disturbances or distractions.

According to aspects and embodiments of the present specification, a processor is configured to perform the following actions, in any sequence:

Switch off the front pointing optical assembly 601, switch off the associated illuminators 608 and/or switch off, blacken or darken presentation of the front view screen 701, Switch off the second side-pointing optical assembly 603, switch off the associated illuminators 628 and/or switch off, blacken or darken presentation of the second side view screen 705, Switch the first side optical assembly 602 from the first working distance to the second working distance by moving the first lens 609 out and instead moving the second lens 611 into the optical path 610, for zooming in, —if the endoscope tip section 600a is being used. Alternatively, switch off, deactivate or disable, such as by cutting electrical power supply, the first side-pointing first optical assembly 602A (having the first working distance) and switch on, activate or enable, such as by allowing electrical power supply, the first side-pointing second optical assembly 602B (having the second working distance), for zooming in, —if the endoscope tip section 600b is being used.

This enables, the front view screen 701 and the second side view screen 705 to be disabled, blackened or darkened while the first side view screen 703 display the magnified polyp image 711" replacing the earlier non-magnified image of the polyp 311.

Figure 8A:
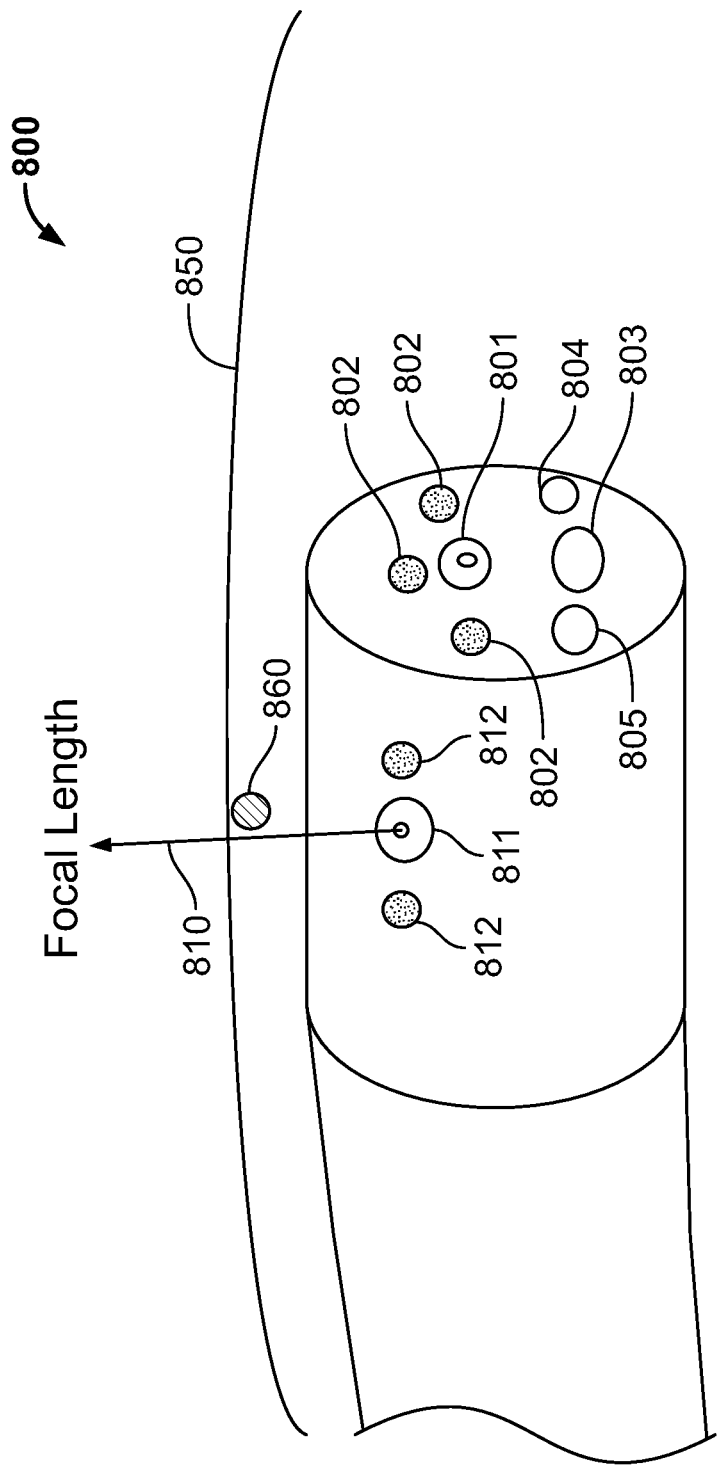
FIG. 8A illustrates a multi-focal side pointing optical assembly within a body cavity and at a distance, from an object of interest, that does not match a working distance of the multi-focal side pointing optical assembly being used to obtain a magnified image of the object of interest.

Reference is now made to FIG. 8A, which shows a perspective view of a multi-focal, multi-camera endoscope tip section, an inner wall of a body cavity and an object of interest, according to certain embodiments. Endoscope tip section 800 (which may be the tip section 600a or 600b of FIGS. 6A, 6B) includes front-pointing viewing element or camera 801, one or more front-pointing illuminators 802, a working channel 803, a fluid injection channel 804, a fluid injection channel 805 for cleaning camera 801 and illuminators 802, a multi-focal side-pointing viewing element 811 and one or more side-pointing illuminators 812. The endoscope tip section 800, in various alternate embodiments, also optionally includes another side-pointing viewing element and associated one or more side-pointing illuminators positioned on the other side opposing the side of the multi-focal viewing element 811.

According to some embodiments, the term 'inner wall of a body cavity', includes, for example, an inner wall of a colon or intestine. The multi-camera endoscope tip section 800 is illustrated in the vicinity of the inner wall of the body cavity 850 that may be a colon wall for example, having an anomaly or object of interest 860 that may require further interrogation. For further interrogation, operation of the multi-focal side-pointing viewing element 811 is shifted from a first working distance, such as that provided by the lens 609 of FIG. 6A or that provided by the first side-pointing first optical assembly 602B of FIG. 6B, to an increased magnification or second working distance, such as that provided by the lens 611 shown on FIG. 6A, for example, or that provided by the first side-pointing second optical assembly 602B of FIG. 6B. In accordance with an aspect, the object of interest 860 may be too close to the multi-focal side pointing viewing element 811 as shown by the arrow 810 that illustrates the increased magnification or second working distance. As illustrated in the figure, since the distance to the object 860 does not match the working distance of the increased magnification lens 611 or the working distance provided by the first side-pointing second optical assembly 602B, zooming in and shifting to the increased magnification working distance may generate a blurry image of the object 860 on the side view screen 703, shown in FIG. 7A.

Figure 8B:
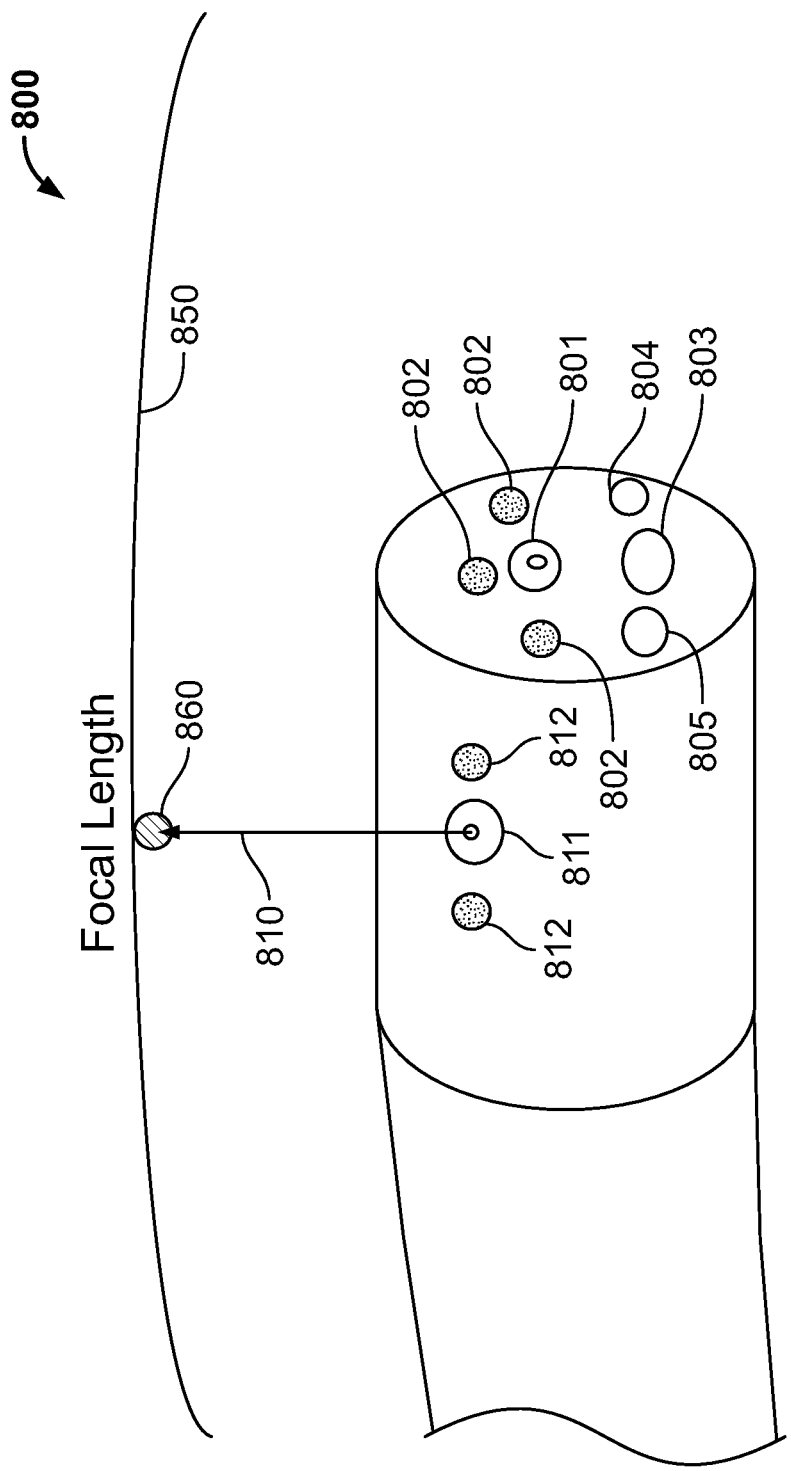
FIG. 8B illustrates the multi-focal side pointing optical assembly of FIG. 8A within an inflated body cavity such that a distance of the multi-focal optical assembly, from the object of interest, approximately matches the working distance of the multi-focal side pointing optical assembly.

Reference is now made to FIG. 8B, which shows a perspective view of the multi-focal, multi-camera endoscope tip section 800 with an inflated colon, according to certain embodiments. In various embodiments, the inner wall of the body cavity 850 is pushed away from the endoscope tip section 800, thereby increasing the distance of the multi-focal side-pointing viewing element 811 to the inner wall, such that the working distance, illustrated by the arrow 810, approximately matches the distance from the side-pointing viewing element 811 to the object of interest 860. In one embodiment, the distance of the multi-focal side-pointing viewing element 811 to the inner wall of the body cavity 850 is increased or adjusted, for example, by injecting gas into the colon through the fluid injection channel 804.

Figure 8C:
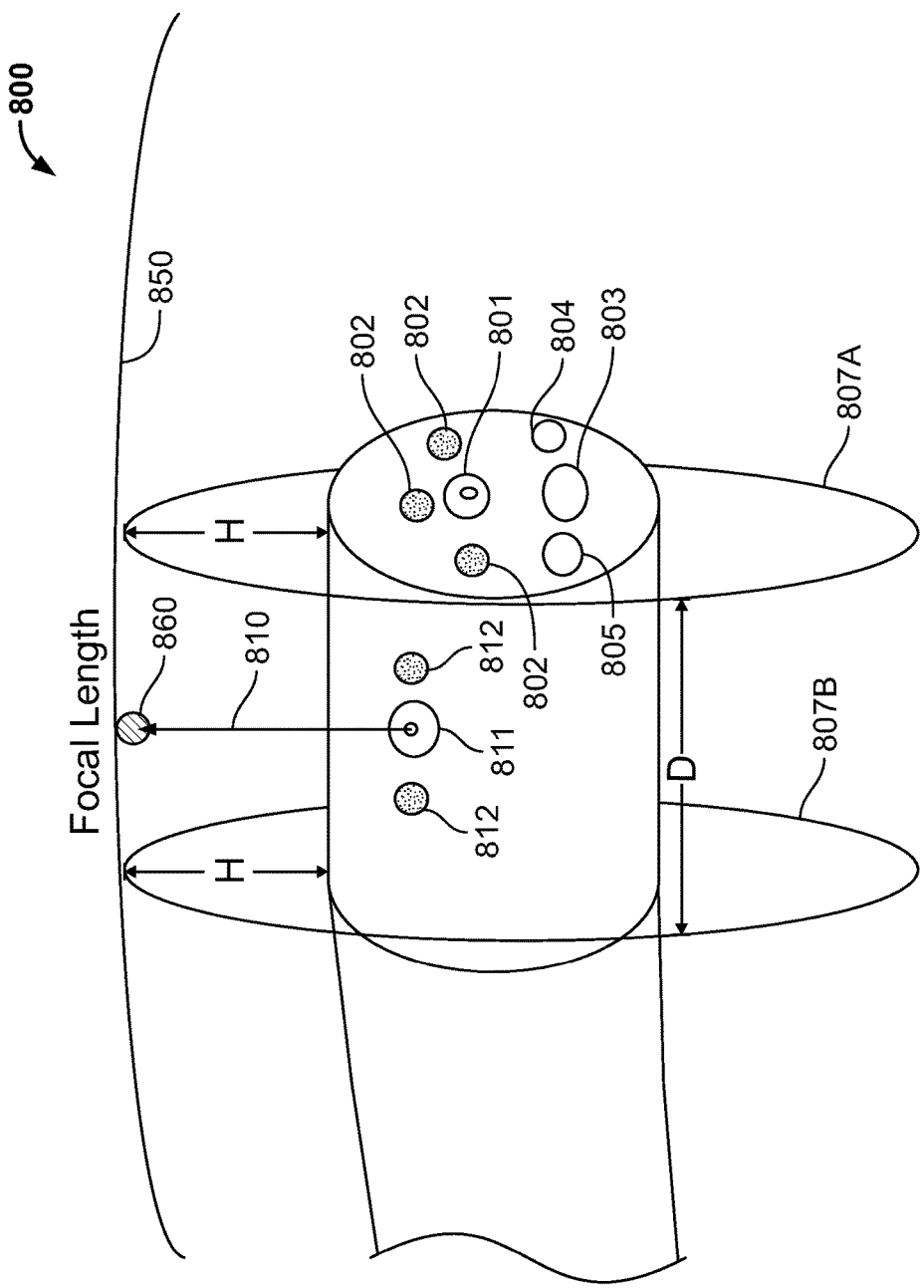
FIG. 8C illustrates the multi-focal side pointing optical assembly of FIG. 8A that deploys first and second distance determining members to position the multi-focal side pointing optical assembly at a distance, from the object of interest, approximately matching the working distance of the multi-focal side pointing optical assembly.

Reference is now made to FIG. 8C, which shows a perspective view of the multi-focal, multi-camera endoscope tip section 800 comprising one or more, preferably three or more, distance determining members configured to contact the inner wall of the body cavity, according to certain embodiments. In accordance with an aspect of the present specification, distance determining members or spacers, such as the spacers 807A and 807B, are pulled radially, outwardly, extended or deployed from the tip section 800 and are configured to maintain a distance between the multi-focal side pointing viewing element 811 to the inner wall of the body cavity 850. While in the present embodiment, two distance determining members 807A, 807B are illustrated in FIG. 8C, a preferred embodiment comprises three or more such distance determining members. In alternate embodiments, one or more distance determining members or spacers are utilized. The first and second distance determining members 807A and 807B are configured to contact the inner wall of the body cavity 450 in order to maintain a constant distance from the multi-focal side-pointing viewing element 811 to the object 860 that matches the increased magnification or second working distance, such as that provided by the lens 611 shown on FIG. 6A, for example, or that provided by the first side-pointing second optical assembly 602B of FIG. 6B. Thus, the distance determining members 807A and 807B are configured, that is sized and/or deployed to a position radially outwardly from the tip section 800, to enable a stable magnified image captured by the multi-focal side-pointing viewing element 811 for display on the side view screen 703 (shown in FIG. 7C).

In various embodiments, the one or more distance determining members 807A and 807B are deployable rings that are mounted on a distal end of the tip section 800 or pulled radially and outwardly from the tip section 800 when triggered or actuated, such as by pushing a button or switch on a handle of an endoscope comprising the endoscope tip section 800, in one embodiment, or by configuring a processor, associated with the endoscope, to automatically deploy the rings when the multi-focal side-pointing viewing element 811 is enabled to obtain magnified images at the second working distance such as that provided by the lens 611 shown on FIG. 6A, for example, or that provided by the first side-pointing second optical assembly 602B of FIG. 6B. In alternate embodiments, the one or more distance determining members 807A, 807B are designed as protrusions or spacers similar to the protrusions 415, 416, 417 of FIG. 4.

In various embodiments, the radially protruding height 'H' of the distance determining members or spacers 807A, 807B ranges between 1.5 to 7 mm. In one embodiment, the radially protruding height 'H' of the one or more distance determining members or spacers 807A, 807B is limited to 2 mm to ensure that the field of view of the viewing element 811 is not distorted by the spacers 807A, 807B. In various embodiments, the one or more distance determining members 807A, 807B are spaced from each other such that a distance 'D' between any two consecutive distance determining members ranges between 8 to 10 mm or 10 to 15 mm.

Figure 9:
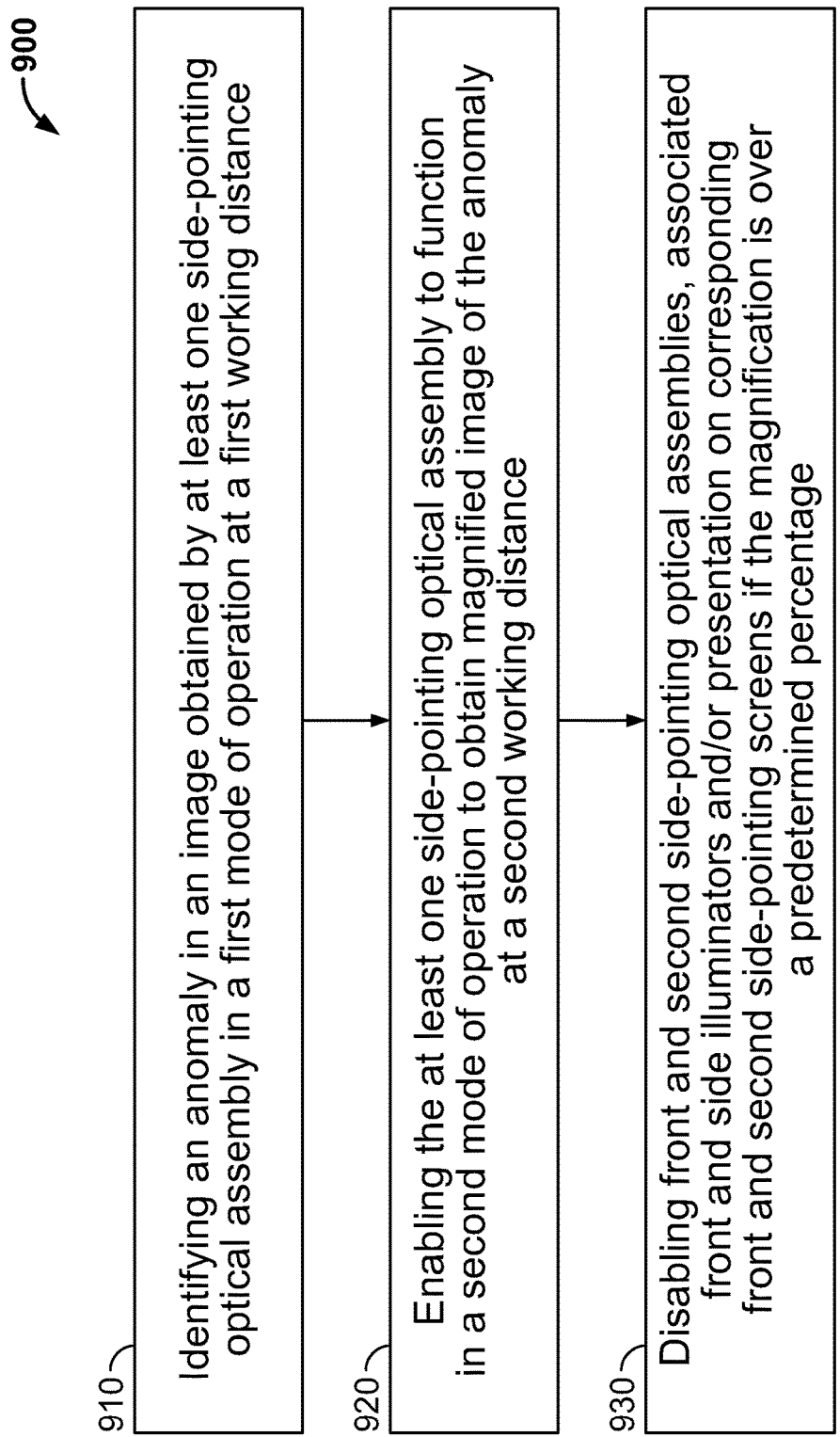
FIG. 9 is a flowchart illustrating a plurality of exemplary steps of a method of obtaining a magnified view of an area or object of interest within a body cavity, such as a colon, using a multi-focal side pointing optical assembly of a multi focal, multi-camera endoscope tip section.

FIG. 9 is a flowchart illustrating a plurality of exemplary steps of a method 900 of obtaining a magnified view of an area or object of interest within a body cavity, such as a colon, using a multi focal, multi-camera endoscope tip section of an endoscope, such as a colonoscope. A processor, associated with the endoscope, is configured to implement the method 900. Referring now to FIGS. 6A, 6B and 9, at step 910 a multi focal, multi-camera endoscope tip section, such as the tip section 600a or 600b, is navigated into a patient's colon in a first mode of operation of at least one multi-focal side-pointing optical assembly (that is, the first side-pointing optical assembly 602 of the tip section 600a or the first side-pointing first optical assembly 602A of the tip section 600b) to identify an anomaly, area or object of interest—such as a polyp. During the first mode of operation the at least one multi-focal side-pointing optical assembly obtains images and/or videos of the colon at a first working distance. The at least one multi-focal side-pointing optical assembly is enabled to function at the first working distance using a first lens 609 or a first side-pointing first optical assembly 602A (while the first side-pointing second optical assembly 602B is disabled) depending upon whether the endoscope tip section 600a or 600b is being used. In one embodiment, the endoscope tip section is operated in the first mode, by default.

The images and/or videos obtained from the at least one multi-focal side-pointing optical assembly, in the first mode of operation, are displayed on a corresponding first side view screen along with an identified anomaly, while the images and/or videos obtained from a front and a second side-pointing optical assemblies are displayed respectively on corresponding front and second side-pointing screens. It should be appreciated that the identified anomaly visible on the first side view screen, as captured by the at least one multi-focal side-pointing optical assembly, may also be simultaneously displayed on the front viewing screen as also captured in an overlapping field of view of the front-pointing optical assembly. In various embodiments, during the first mode of operation a magnification of 100× to 6× of the captured image of the anomaly is enabled for the first working distance.

At step 520, the processor enables the at least one multi-focal side-pointing optical assembly to function in a second mode of operation in order to obtain and display a magnified image, comprising the identified anomaly, on the first side view screen. During the second mode of operation the at least one multi-focal side-pointing optical assembly obtains the magnified image at a second working distance. The at least one multi-focal side-pointing optical assembly is enabled to function at the second working distance by switching to using a second lens 611 or by activating a first side-pointing second optical assembly 602B (while simultaneously disabling the first side-pointing first optical assembly 602A) depending upon whether the endoscope tip section 600a or 600b is being used. In various embodiments, during the second mode of operation the enabled magnification of the captured image of the anomaly ranges between 250× to 100× for the second working distance.

In accordance with an embodiment, a distance between the at least one multi-focal side-pointing optical assembly and the identified anomaly or object of interest is maintained by deploying, one or more distance determining members, such as the members 807A and 807 of FIG. 8C, radially outwardly from a distal end of the endoscope tip section and advancing the tip section until the one or more distance determining members contact the anomaly or the inner wall of the colon thereby maintaining the distance to approximately the second working distance. In this embodiment, a radially outwardly deployed expanse or extent of the distance determining members, that are rings in one embodiment, can be varied by retracting or deploying them partially or fully. In other embodiments, the distance determining members are affixed to the distal end and therefore provide a fixed outward radial expanse or extent, approximately matching the second working distance.

In accordance with another embodiment, the body cavity, such as the colon, is inflated in order to push away the object of interest lying on the wall of the colon from the endoscope tip section, thereby increasing the distance of the at least one multi-focal side-pointing optical assembly to the inner wall, such that the working distance approximately matches the distance from the multi-focal side-pointing optical assembly to the object of interest. In one embodiment, the distance of the at least one multi-focal side-pointing optical assembly to the inner wall of the body cavity is increased or adjusted, for example, by injecting gas into the colon through a fluid injection channel located at the distal end of the tip section.

At step 530, when the magnification of the magnified image on the first side view screen is over a predetermined percentage, the processor performs any one or a combination of the following actions: a) turns off or disables the front and second side-pointing optical assemblies while the illuminators associated with the font and second side-pointing optical assemblies are switched on and the front and second side pointing screens also continue to stay switched on, b) switch off the front and second side illuminators associated with the front and second side-pointing optical assemblies while the front and second side-pointing optical assemblies continue to generate live images and/or video streams and the front and second side pointing screens also continue to stay switched on, and/or c) switch off, darken or blacken presentation of the images and/or videos on the front and second side-pointing screens while the front and second side-pointing optical assemblies continue to generate live images and/or video streams and the illuminators associated with the font and second side-pointing optical assemblies also continue to stay switched on, when the magnification of the magnified image on the first side view screen is over a predetermined percentage. In some embodiments, the predetermined magnification percentage is about 30% or more.

If required, a surgical tool may be inserted through a side service or working channel of the endoscope in order to remove, treat and/or extract a sample of the anomaly or object of interest or its entirety for biopsy, while viewing the magnified image. In accordance with an embodiment, actuating a button or switch on a handle of the endoscope prompts the processor to switch the endoscope tip section from the first mode of operation to the second mode of operation.

It should be appreciated that while the endoscope tip sections 100a, 100b (FIGS. 1, 2) illustrate a single multi-focal optical assembly configured as the front-pointing optical assembly 101 (or 101A, 101B) and the endoscope tip sections 600a, 600b (FIGS. 6A, 6B) illustrate a single multi-focal optical assembly configured as the first side-pointing optical assembly 602 (or 602A, 602B), in various alternate embodiments a multi-focal, multi-camera endoscope tip section may comprise more than one multi-focal optical assemblies. For example, various embodiments of the endoscope tip section may comprise at least two and up to three multi-focal optical assemblies configured as front-pointing and first and/or second side-pointing optical assemblies. In such endoscope tip sections comprising multiple multi-focal optical assemblies, the multi-focal optical assembly that is best suited, positioned or oriented to observe an anomaly in magnified or microscopic view is enabled to function in the second mode of operation to display the magnified view on a corresponding screen, while the remaining optical assemblies and/or the corresponding screens are disabled and/or darkened.

Figure 10A:
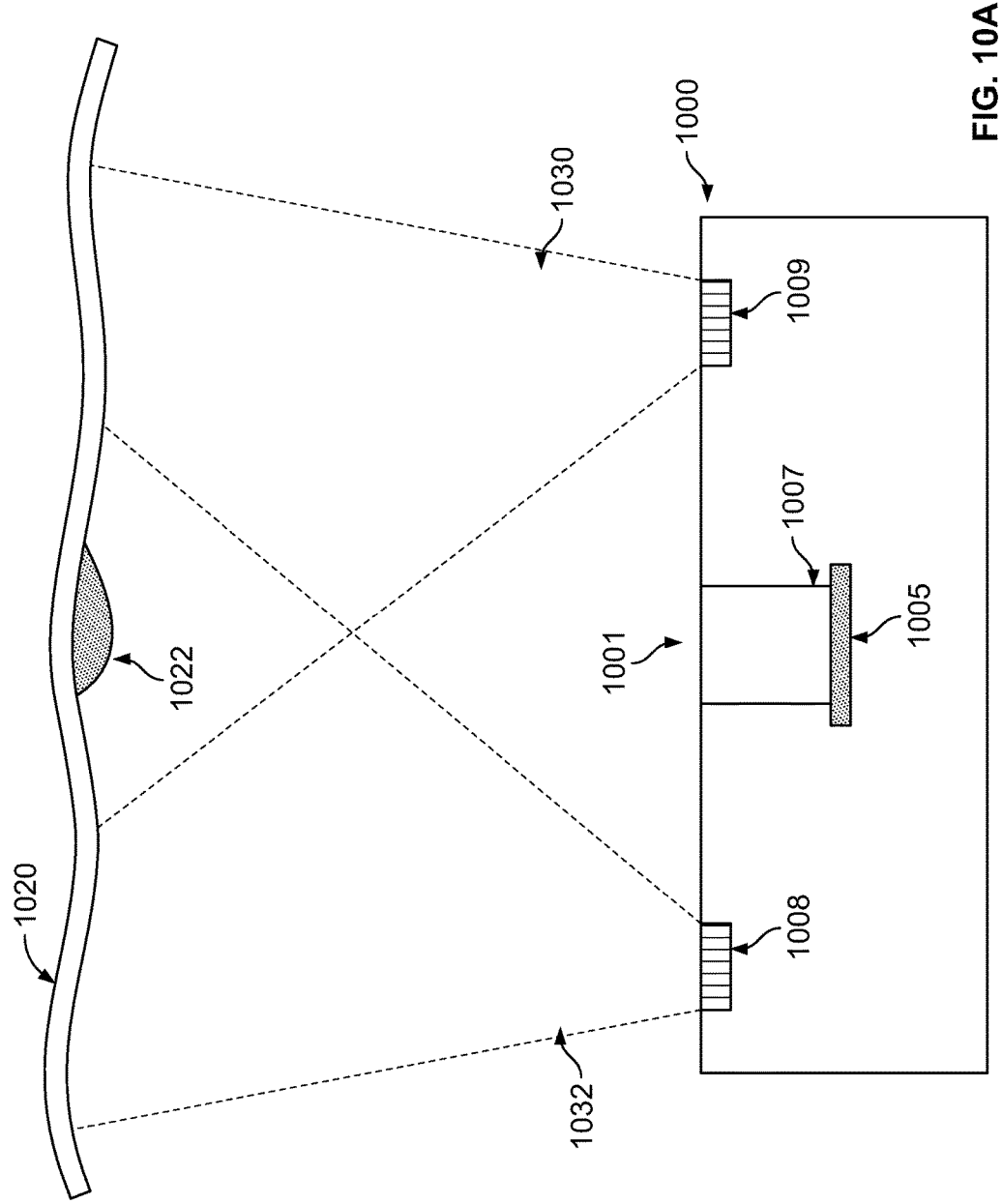
FIG. 10A illustrates an endoscope tip section illuminating an anomaly, within a body cavity, at a first working distance.
Figure 10B:
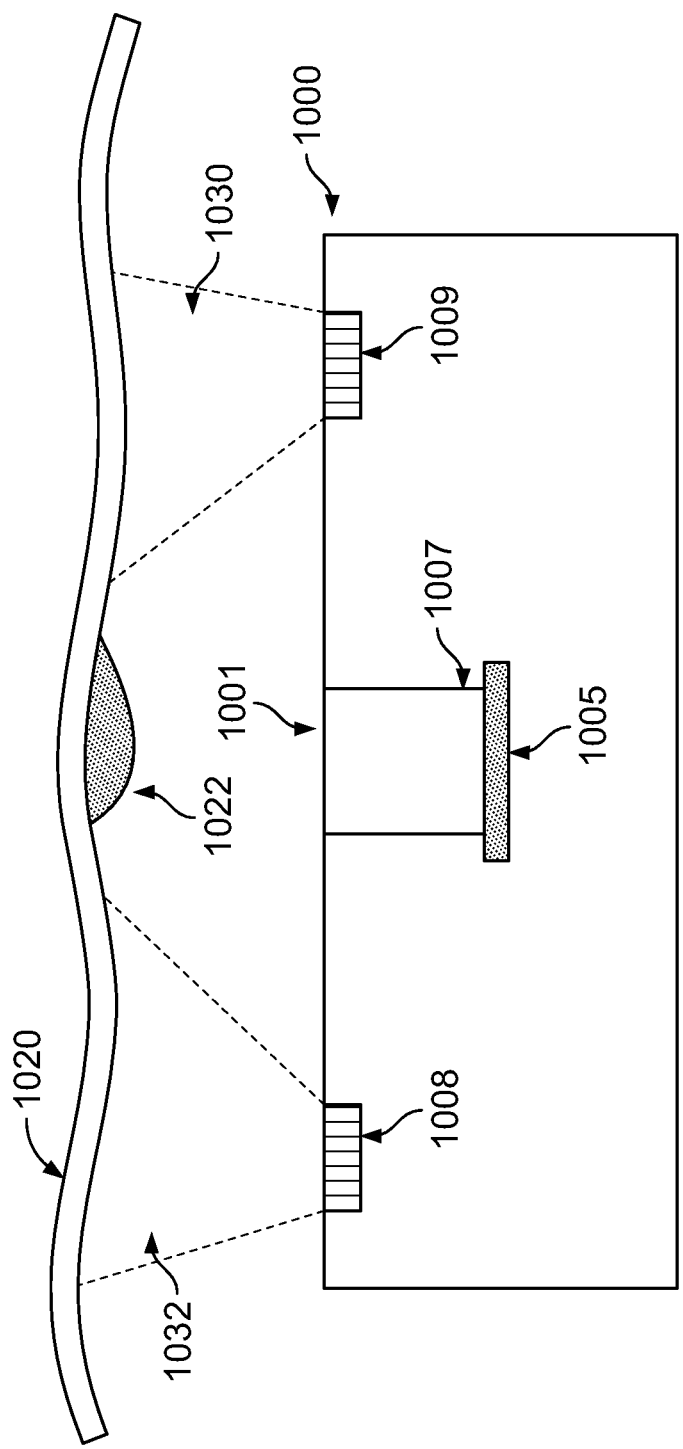
FIG. 10B illustrates the endoscope tip section of FIG. 10A failing to illuminate the anomaly at a second working distance.

FIGS. 10A and 10B illustrate an endoscope tip section 1000 used to view and obtain image and/or video of an internal wall 1020 of a body cavity, such as a colon, having an anomaly or object of interest 1022, such as a polyp. The tip section 1000 has an optical assembly 1001 comprising an image sensor 1005 mounted on an integrated circuit board, a lens assembly 1007 mounted on the image sensor 1005 to capture images and one or more associated illuminators, such as illuminators 1008 and 1009. The first illuminator 1008 generates a first field of illumination 1030 while the second illuminator 1009 generates a second field of illumination 1032.

As shown in FIG. 10A, while the tip section 1000 is being navigated through the body cavity, the optical assembly 1001 is located at a first working distance from the polyp 1022 at which the first and second fields of illumination sufficiently illuminate the polyp 1022 to enable the image sensor 1005 and lens assembly 1007 to capture images of the polyp 1022. Once the polyp 1022 has been identified the endoscope tip section 1000 is now moved closer to the polyp 1022 at a second working distance in order to obtain a magnified image or view of the polyp 1022 (for example, to closely analyze the polyp 1022), as shown in FIG. 10B. The second working distance is shorter that the first working distance and, as shown in FIG. 10B, at the second (shorter) working distance the first and second fields of illumination 1030, 1032 fail to illuminate the polyp 1022, partially or fully. Thus, even if the lens assembly 1007 includes optical elements (such as lenses) providing a working distance or field of view that suffices capturing images of the polyp 1022 at the second working distance, a lack of proper illumination diminishes the ability of viewing or obtaining images of the polyp 1022.

Thus, in accordance with an aspect, the present specification discloses systems and methods to adjust, redirect or redistribute the illumination or fields of view of one or more illuminators to facilitate sufficient illumination of an object of interest for viewing or obtaining a magnified image and/or video of the object of interest using an optical assembly.

FIGS. 11A through 11J illustrate various embodiments of a cross-section of an endoscope tip section, 1100a through 1100g, of an endoscope having at least one optical assembly, associated one or more illuminators and associated light adjusting components. It should be appreciated that the at least one optical assembly (along with the associated illuminators and light adjusting components) may be configured as a front-pointing, a first side-pointing and/or a second side-pointing optical assembly. Thus, in various embodiments, the endoscope tip section is a multi-focal, multi-camera tip section comprising one, two and up to three optical assemblies configured as front-pointing, first side-pointing and/or second side-pointing optical assemblies each having a field of view (FOV) ranging between 150 to 170 degrees, in various embodiments. Also, in various embodiments of the multi-camera tip section comprising up to three optical assemblies configured as front-pointing, first side-pointing and/or second side-pointing optical assemblies a focal length of the front-pointing optical assembly is on the order of 1.1 mm while that of the first and/or second side-pointing assemblies is on the order of 1.0 mm. Also, in some embodiments, the first and/or second side-pointing assemblies are positioned such that their optical axes are at a distance ranging between 6 mm and 10 mm from a distal end of the endoscope.

Figure 11A:
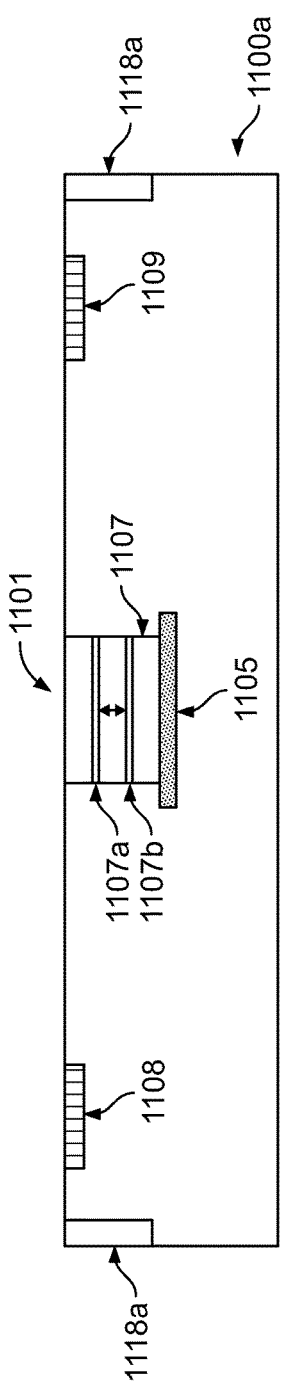
FIG. 11A illustrates an endoscope tip section with an embodiment of a multi-focal optical assembly in a first mode of operation and a first type of light adjusting components refracted in a first mode of illumination.
Figure 11B:
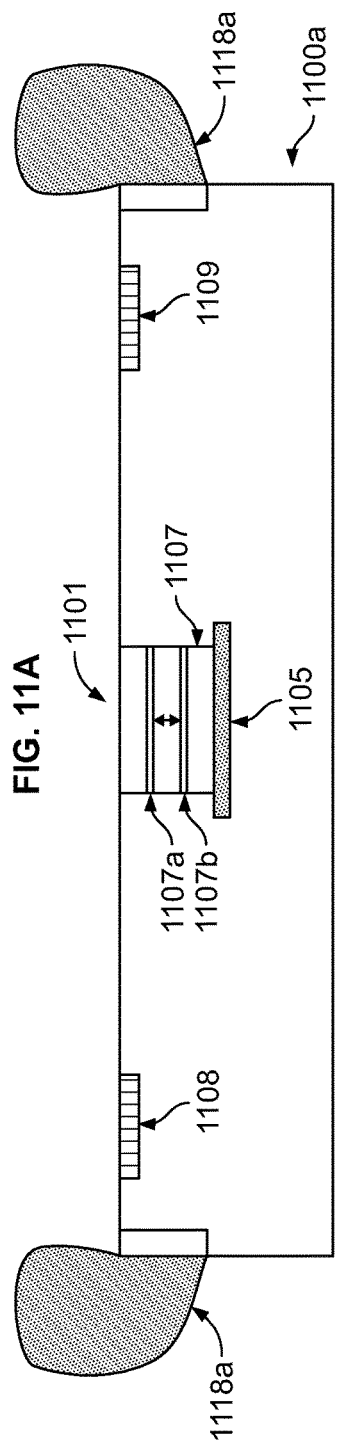
FIG. 11B illustrates the endoscope tip section of FIG. 11A with the multi-focal optical assembly in a second mode of operation and the first type of light adjusting components deployed in a second mode of illumination.

FIGS. 11A and 11B illustrate an endoscope tip section 1100a, in accordance with a first embodiment, with at least one multi-focal optical assembly 1101 comprising an image sensor 1105 mounted on an integrated circuit board, a lens assembly 1107 mounted on the image sensor 1105 and including a first lens 1107a and a second lens 1107b and one or more illuminators, such as first and second illuminators 1108, 1109.

A distance between the first and second lenses 1107a, 1107b is adjustable to enable the optical assembly 1101 (or the lens assembly 1107) to change from having a first working distance or focal length to having a second working distance or focal length. It should be appreciated that in this embodiment, both the lenses 1107a, 1107b are positioned such that they have a common or same optical path or axis. The first working distance is associated with a typical or normal working distance when the endoscope tip section 1100a is being navigated through a body cavity, such as a colon. The second working distance is associated with a microscopic working distance, shorter than the normal or first working distance, when the endoscope tip section 1100a is moved closer to an identified anomaly or object of interest (for analysis) in order to obtain a magnified image of the anomaly, such as a polyp.

In accordance with the first embodiment, the endoscope tip section 1100a also includes a first and a second light adjusting components 1118a that are shown in refracted configuration in FIG. 11A and in deployed configuration in FIG. 11B. In an embodiment, the light adjusting components 1118a are positioned on either side of the optical assembly 1101 such that the optical assembly 1101 along with the associated illuminators 1108, 1009 lie between the first and second light adjusting components 1118a. In an embodiment, the light adjusting components 1118a have a lambertian reflectance surface configured to scatterly or diffusely reflect light. Persons of ordinary skill in the art should appreciate that a lambertian reflectance is the property that defines an ideal "matte" or diffusely reflecting surface. The apparent brightness of a Lambertian surface to an observer is the same regardless of the observer's angle of view. In an embodiment, the light adjusting components 1118a are etched with lambertian coating such as, but not limited to, Labsphere's Spectralon® or Spectraflect® range of coating materials.

In one embodiment, the light adjusting components 1118a are balloons that are inflatable for deployment or protrusion and are electrically and/or mechanically actuatable. In another embodiment, the light adjusting components 1118a are screens initially rolled into spiral, in refracted configuration, and later expanded in deployed configuration.

During an endoscopic procedure while a physician navigates the endoscope tip section 1100a through the body cavity with the optical assembly 1101 providing the first working distance or focal length, the light adjusting components 1118a are in retracted configuration so that light emitted from the first and second illuminators 1108, 1109 directly light up or illuminate the anomaly (as shown in FIG. 10A) in a first mode of illumination. Once the anomaly is identified, the endoscope tip section 1100a is moved closer to the anomaly, the distance between the first and second lenses 1107a, 1107b is adjusted to enable the optical assembly 1107 to provide the microscopic or second working distance and the light adjusting components 1118a (that are balloons in one embodiment) are protruded or deployed (such as by inflating the balloons) so that light rays emanating from the illuminators 1108, 1109 are reflected or redirected into a plurality of oblique light rays that fall on the anomaly in a second mode of illumination. Thus, the oblique rays, in the second mode of illumination, sufficiently light up the anomaly for viewing and/or capturing magnified image of the anomaly at the second working distance.

In one embodiment, the size of the balloons and/or amount of inflation of the balloons is such that when inflated and thus deployed, the balloons enable the multi-focal optical assembly 1101 to be at a distance, from the anomaly, that approximately matches the second working distance or focal length.

Figure 11C:
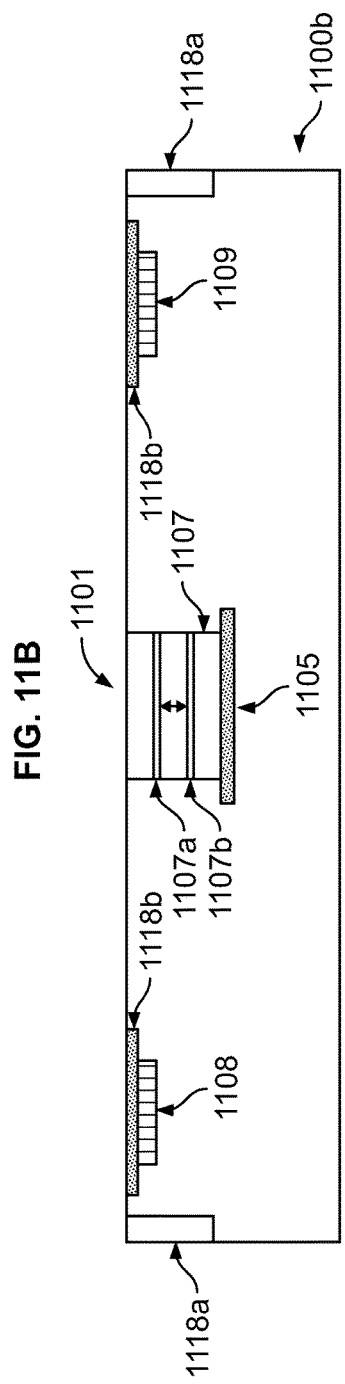
FIG. 11C illustrates an endoscope tip section with a multi-focal optical assembly in the first mode of operation and first and second types of light adjusting components in the first mode of illumination.

FIG. 11C illustrates an endoscope tip section 1100b in accordance with a second embodiment. In the second embodiment, the multi-focal optical assembly 1101 and the associated illuminators 1108, 1109 are similar to the first embodiment of FIGS. 11A and 11B in that the light adjusting components 1118a are included. Additionally, in the second embodiment, first and second light adjusting components 1118b are positioned over the light emitting surfaces of the first and second illuminators 1108, 1109 such that light emitted by the illuminators 1108, 1109 must impinge and pass through the light adjusting components 1118b.

In various embodiments, the light adjusting components 1118b include light diffusers such as, but not limited to, liquid crystal transmissive screens, movable translucent and diffuser films or quantum well diffusers. Examples of liquid crystal transmissive screens or movable translucent and diffuser films comprise polymer dispersed liquid crystal films, also referred to as PDLC films, having microdroplets of a liquid crystal material dispersed within a transparent polymeric matrix. Transparent electrodes are applied to opposite surfaces of the film. In the absence of an electric field, the liquid crystal microdroplets diffuse light, so that the film is translucent. However, an electric field applied between the electrodes orients the liquid crystal molecules to allow the film to transmit light without diffusion, so that the film becomes transparent. Alternatively, the PDLC films may be configured such that in the absence of an electric field, the liquid crystal microdroplets transmit light without diffusion so that the film is transparent. However, an electric field applied between the electrodes orients the liquid crystal molecules to diffuse or scatter light so that the film is translucent.

During the first mode of illumination, when the physician navigates the endoscope tip section 1100b through the body cavity with the optical assembly 1101 providing the first working distance or focal length—the light adjusting components 1118a are refracted and the components 1118b allow passage of light with low or no diffusion. However, during the second mode of illumination, when the physician moves the endoscope tip section 1100b closer to the anomaly for magnified view or image capture with the optical assembly 1101 providing the second working distance—the light adjusting components 1118b allow passage of light with high scatter or diffusion and/or the light adjusting components 1118a are in deployed configuration to diffusely reflect light. Advantageously, scattered or diffused light results in a plurality of oblique rays of illumination that are desired for microscopic imagery at the second working distance.

Figure 13A:
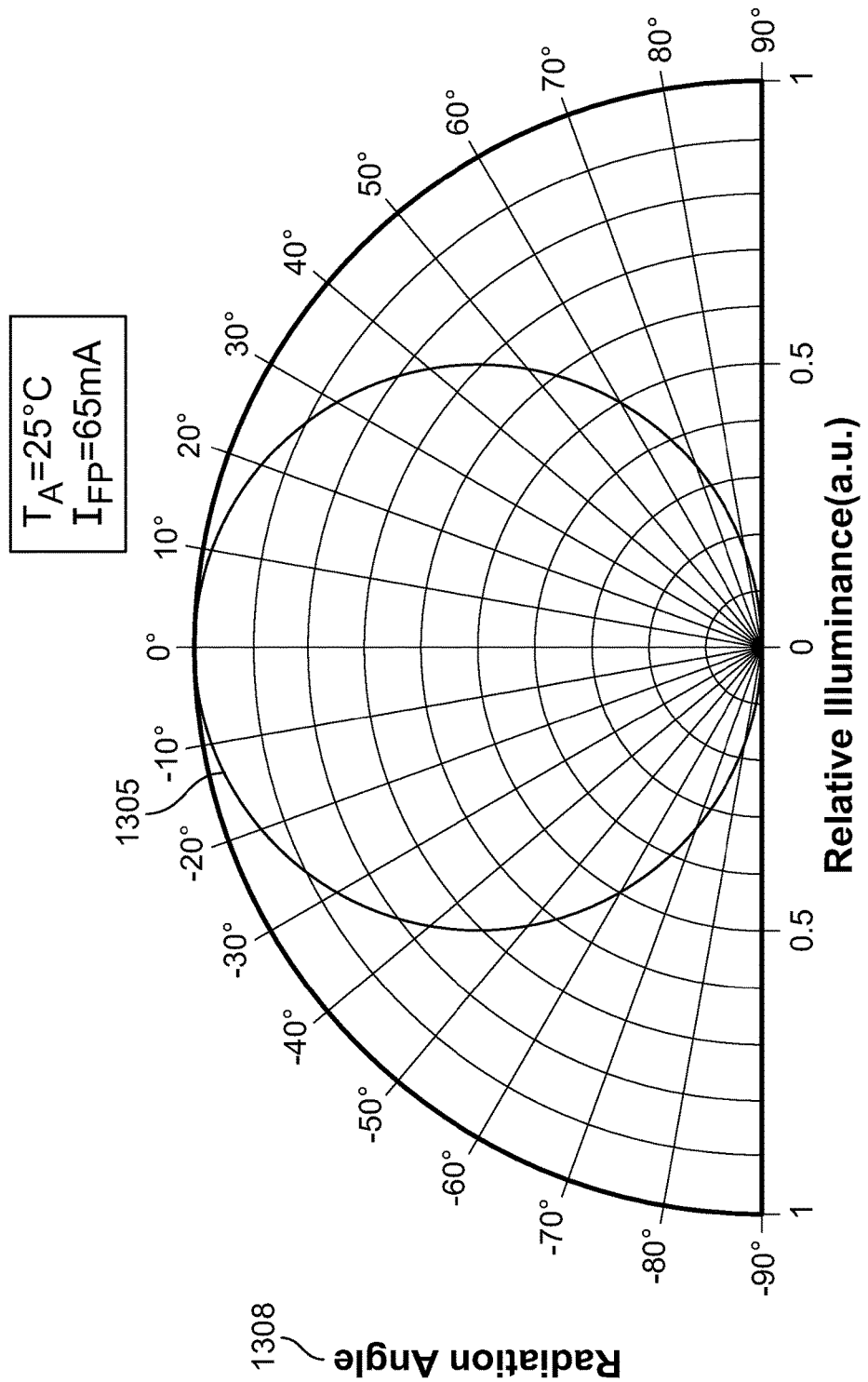
FIG. 13A shows a graph illustrating a variation of relative illuminance with reference to a radiation angle for a light diffuser without application of an electrical field.
Figure 13B:
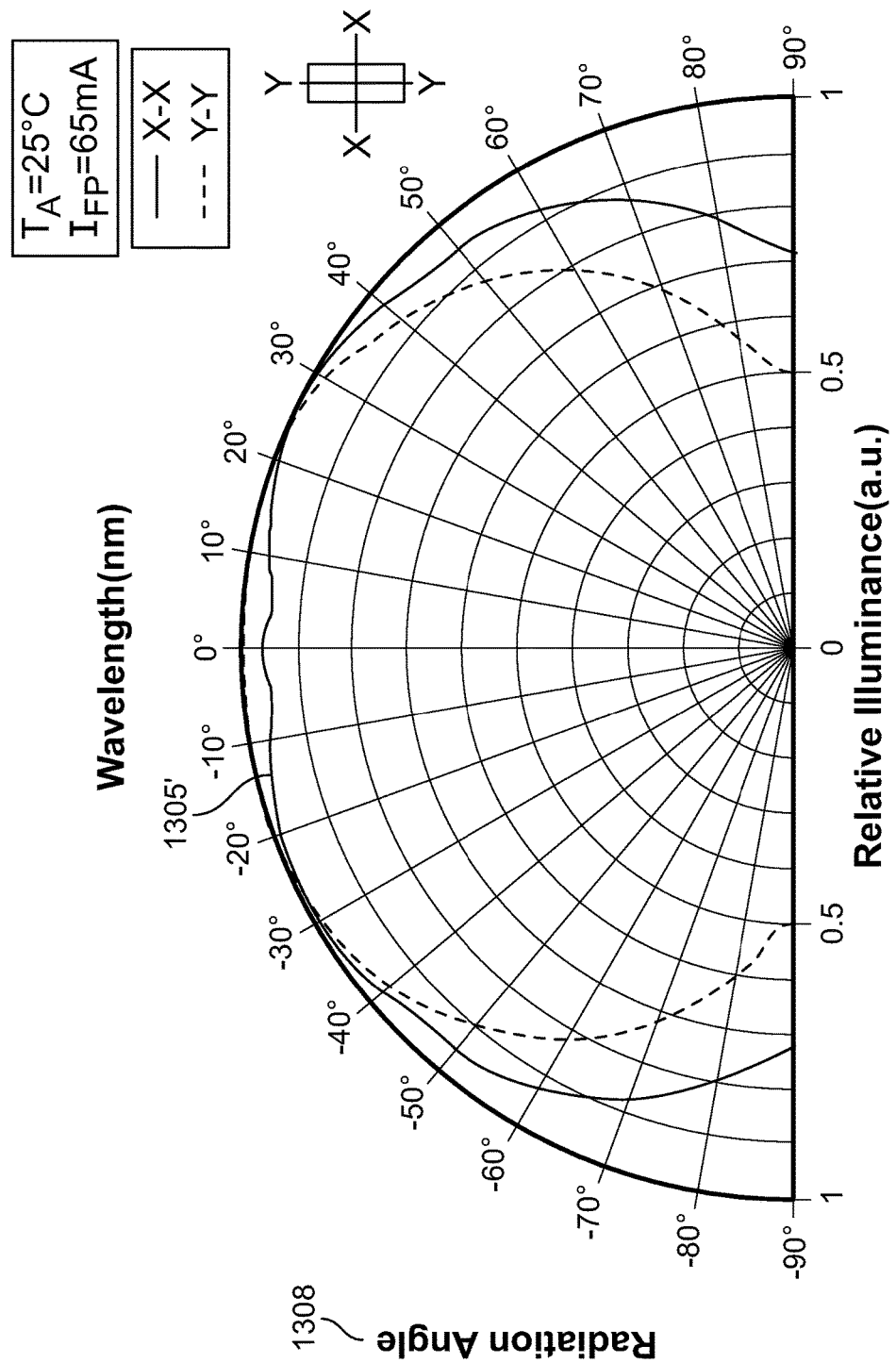
FIG. 13B shows a graph illustrating a variation of relative illuminance with reference to a radiation angle for the light diffuser with application of an electric field.

Advantageously, diffused light has a wide illumination angle. According to some embodiments, an illumination angle of diffused light is nearly 180°. According to some embodiments, an illumination angle of diffused light ranges between 120° and 180°. FIG. 13A shows a graph illustrating a variation of relative illuminance 1305 with reference to a radiation angle 1308 in polar coordinates for a light diffuser, such as the light adjusting components 1118b when no electrical field is applied to the light diffuser. In one embodiment, the light diffuser is a PDLC film that is otherwise transparent to light but diffuses or scatters light when an electric field is applied to it. As discussed earlier in this specification, PDLC films have microdroplets of a liquid crystal material dispersed within a transparent polymeric matrix. Every liquid crystal microdroplet has separate molecules of liquid crystal with a typical size 5-10 µm of about the wavelength of light. Activation of the electrical field changes condition of light polarization and light scattering too. Thus, as shown in FIG. 13B, on application of an electric field to the PDLC film causes the relative illuminance 1305' of light to spread or scattered over a wider radiation angle 1308 compared to the earlier illuminance spread 1305.

Figure 11D:
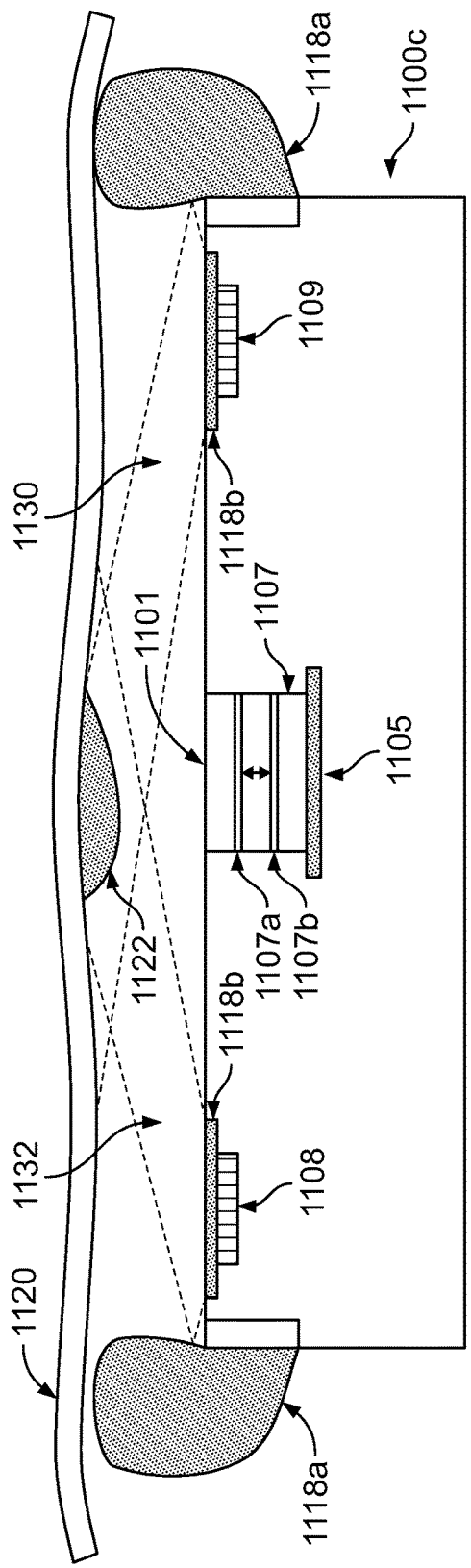
FIG. 11D illustrates the endoscope tip section of FIG. 11C with the multi-focal optical assembly in the second mode of operation and at least one of the first and second types of light adjusting components in the second mode of illumination.

FIG. 11D illustrates an endoscope tip section 1100c in accordance with a third embodiment which is similar to the second embodiment (1100b) in that the tip section 1100c includes both types of light adjusting components 1118a, 1118b. FIG. 11D specifically illustrates the second mode of illumination when the endoscope tip section 1100c is moved closer to the anomaly 1122, located at an internal wall 1120 of a body cavity, with the multi-focal optical assembly 1101 adjusted to provide the second working distance. As shown, in the second mode of illumination, the light adjusting components 1118a in deployed configuration diffusely reflect light of the illuminators 1108, 1109 and the light adjusting components 1118b also allow passage of light from the illuminators 1108, 1109 with high scatter or diffusion to form a plurality of oblique rays 1130, 1132 that illuminate the anomaly 1122. It should be appreciated, that in various alternate embodiments, while both types of light adjusting components 1118a, 118b are provided in the endoscope tip section any one or both types of light adjusting components 1118a, 1118b can be actuated and utilized to illuminate the anomaly for microscopic visualization and imagery. Thus, according to various embodiments, the light adjusting components 1118a, 1118b are configured to adjust, redirect, diffusely scatter or reflect light for providing dark-field illumination for microscopic imagery. Dark-field illumination is achieved by providing light, as oblique rays, characterized with acute angles relative to the anomaly such that direct reflection of the light from the anomaly to the multi-focal optical assembly is minimal.

FIGS. 11E and 11F illustrate an endoscope tip section 1100d, in accordance with a fourth embodiment which is similar to the first embodiment (1100a) with a difference that the lens assembly 1107 comprises interchangeable first and second lenses 1107a, 1107b. Thus, during the first mode of illumination, illustrated by FIG. 11E, the multi-focal optical assembly 1101 is enabled to provide the first working distance or focal length by having the first lens 1107a positioned in the optical path or axis of the lens assembly 1107 while the light adjusting components 1118a (such as balloons) are in retracted configuration. However, during the second mode of illumination, illustrated by FIG. 11F, the optical assembly 1101 is enabled to provide the second working distance or focal length by moving the first lens 1107a out from the optical path and inserting the second lens 1107b into the optical path or axis while the light adjusting components 1118a are in deployed configuration (such as, by inflating the balloons).

FIG. 11G illustrates an endoscope tip section 1100e, in accordance with a fifth embodiment which is similar to the third embodiment (1100c) with a difference that the lens assembly 1107 comprises interchangeable first and second lenses 1107a, 1107b as illustrated in the embodiments of FIG. 11E, 11F. Referring now to FIG. 11G, during the first mode of illumination, the multi-focal optical assembly 1101 is enabled to provide the first working distance or focal length by having the first lens 1107a positioned in the optical path or axis of the lens assembly 1107 while the light adjusting components 1118*a* (such as balloons) are in refracted configuration and the light adjusting components 1118*b* (such as, liquid crystal transmissive screens) are enabled to allow passage of light therethrough with low or no diffusion or scatter. However, during the second mode of illumination the optical assembly 1101 is enabled to provide the second working distance or focal length by moving the first lens 1107*a* out from the optical path and inserting the second lens 1107*b* into the optical path or axis while the light adjusting components 1118*a* are in deployed configuration and/or the light adjusting components 1118*b* are enabled to allow passage of light therethrough with high diffusion or scatter.

FIGS. 11H and 11I illustrate an endoscope tip section 1100*f*, in accordance with a sixth embodiment which is similar to the third embodiment (1100*c*) with a difference that the tip section 1100*f* comprises first and second multi-focal optical assemblies 1101, 1101' (together referred to as a 'composite multi-focal optical assembly') comprising corresponding image sensors 1105, 1105' mounted on respective integrated circuit boards, corresponding lens assemblies 1107, 1107' mounted on the respective image sensors 1105, 1105' and one or more associated illuminators, such as the illuminators 1108, 1109. The first lens assembly 1107 enables the optical assembly 1101 to provide the first working distance or focal length. The second lens assembly 1107' enables the optical assembly 1101' to provide the second working distance or focal length. Referring now to FIG. 11H, during the first mode of illumination, the first optical assembly 1101 is enabled to provide the first working distance or focal length, the second optical assembly 1101' is disabled while the light adjusting components 1118*a* (such as balloons) are in retracted configuration. However, during the second mode of illumination, as illustrated in FIG. 11I, the second optical assembly 1101' is enabled to provide the second working distance or focal length, the first optical assembly 1101 is disabled while the light adjusting components 1118*a* are in deployed configuration.

FIG. 11J illustrates an endoscope tip section 1100*g*, in accordance with a seventh embodiment which is similar to the third embodiment (1100) with a difference that the tip section 1100*g* comprises first and second optical assemblies 1101, 1101' ('composite optical assembly') similar to the embodiments of FIGS. 11H, 11I. As shown in FIG. 11J, during the first mode of illumination, the first optical assembly 1101 is enabled to provide the first working distance or focal length, the second optical assembly 1101' is disabled while the light adjusting components 1118*a* (such as balloons) are in retracted configuration and the light adjusting components 1118*b* (such as, liquid crystal transmissive screens) are enabled to allow passage of light therethrough with low or no diffusion or scatter. However, during the second mode of illumination the second optical assembly 1101' is enabled, the first optical assembly 1101 is disabled while the light adjusting components 1118*a* are in deployed configuration and/or the light adjusting components 1118*b* are enabled to allow passage of light therethrough with high diffusion or scatter.

In various embodiments, during the second mode of illumination the light adjusting components 1118*a* and/or 1118*b* are manually activated by a physician by actuating at least one button or switch on a handle of the endoscope to trigger an associated processor to enable the endoscope tip section (1100*e*, 1100*g*) to function in the second mode of illumination. In another embodiment, the processor is configured to automatically enable the endoscope tip section to function in the second mode of illumination.

In some alternate embodiments, illumination intensity of the illuminators is adjustable. According to some embodiments, at least one illuminator is switched off while other illuminators are switched on. According to further embodiments, the endoscope tip section comprises multiple illuminators that are located at different distances from the multi-focal optical assembly. Advantageously, in the second mode of illumination, illuminators that are located in close proximities to the multi-focal optical assembly are switched off and while illuminators that are located relatively farther from the multi-focal optical assembly are switched on, thereby, result in a reduction of direct light reflection from the anomaly to the multi-focal optical assembly.

Figure 12:
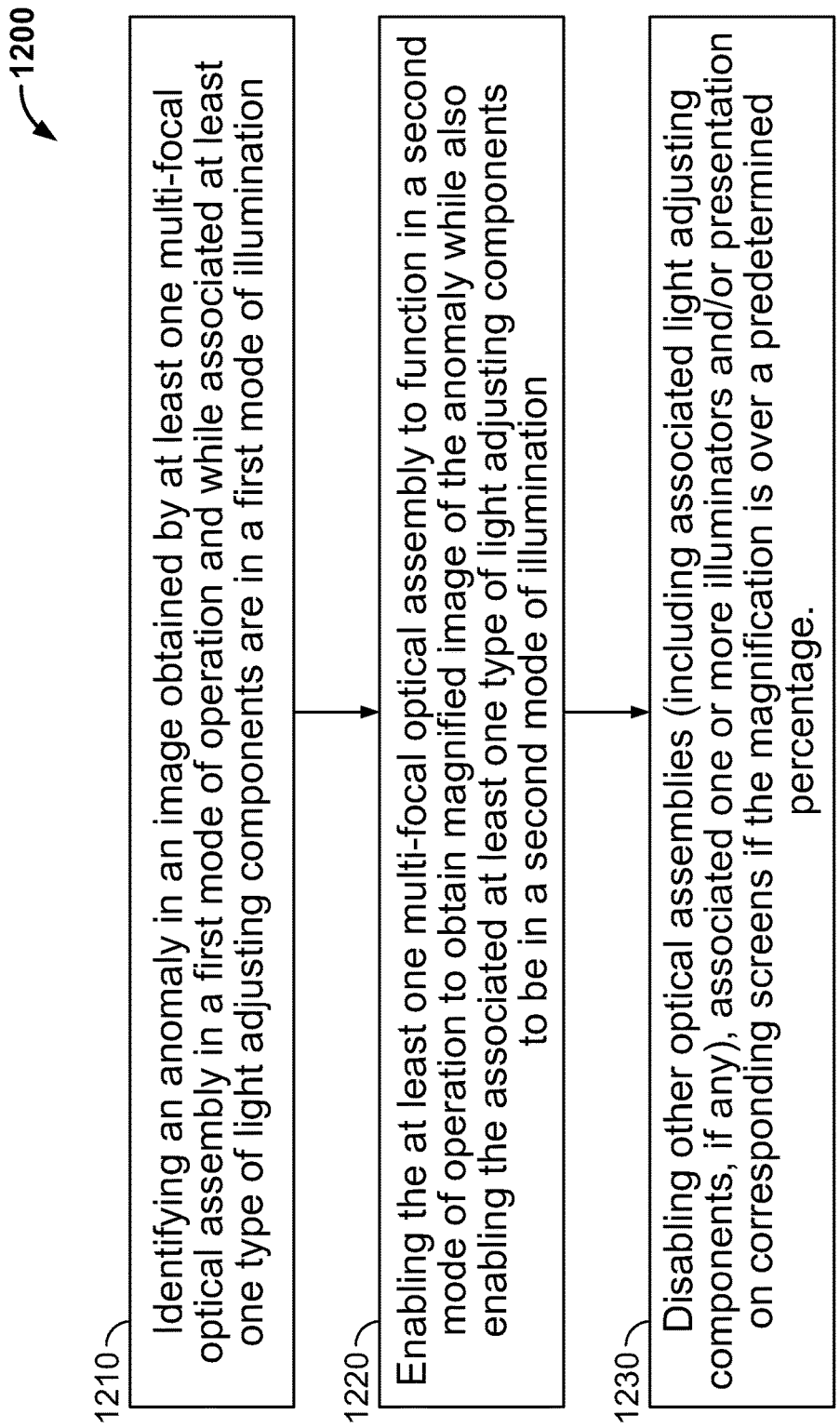
FIG. 12 is a flowchart illustrating a plurality of exemplary steps of a method of obtaining a magnified view of an area or object of interest within a body cavity, such as a colon, using a multi focal, multi-camera endoscope tip section equipped with at least one of first and second types of light adjusting components.

FIG. 12 is a flowchart illustrating a plurality of exemplary steps of a method 1200 of obtaining a magnified view of an area or object of interest within a body cavity, such as a colon, using a multi focal, multi-camera endoscope tip section of an endoscope, such as a colonoscope, in accordance with various embodiments. A processor, associated with the endoscope, is configured to implement the method 1200.

Referring now to FIGS. 11A through 11J and 12, at step 1210 a multi focal, multi-camera endoscope tip section, such as any one of the tip section 1100*a* through 1100*g*, is navigated into a patient's colon. In various embodiments, the endoscope tip section comprises at least one and up to three multi-focal optical assemblies. The one or more multi-focal optical assemblies are configured as a front-pointing, first and/or second side-pointing optical assemblies in various embodiments. As illustrated in FIGS. 11A through 11J, the at least one multi-focal optical assembly is: a) configured to have at least two lenses, both of which are positioned in the same optical path or axis of the at least one optical assembly, to provide a first or a second working distance or focal length by adjusting a distance between the two lenses, b) configured to have at least two lenses that are interchangeably moved into the optical path or axis of the at least one optical assembly to provide the first and the second working distance or focal length, or c) configured as a 'composite optical assembly' comprising a first optical assembly having a first lens (or a plurality of lenses) to provide the first working distance or focal length and a second optical assembly having a second lens (or a plurality of lenses) to provide the second working distance or focal length. As discussed earlier in this specification, the first working distance or focal length is associated with a first mode of operation of the at least one multi-focal optical assembly while navigating the endoscope tip section through the colon for an initial identification of an anomaly, area or object of interest. The second working distance or focal length is associated with a second mode of operation of the at least one multi-focal optical assembly while observing, analyzing, viewing and/or obtaining a magnified image of the identified anomaly, area or object of interest.

Also, as illustrated in FIGS. 11A through 11J, the at least one multi-focal optical assembly is associated with one or more illuminators and also associated with a) light adjusting components of a first type, such as the components 1118*a* comprising, for example, inflatable balloons having Lambertian reflectance surfaces which, in a first mode of illumination, are in a refracted configuration and which when deployed, in a second mode of illumination, diffusely scatter light of the one or more illuminators so that light emanating from the one or more illuminators is diffusely reflected in a plurality of oblique rays towards the identified anomaly, area or object of interest, and/or b) light adjusting components of a second type, such as the components 1118*b* comprising light diffusers such as, but not limited to, liquid crystal transmissive screens, movable translucent and diffuser films or quantum well diffusers. In the first mode of illumination the light adjusting components allow passage of light therethrough with no or relatively low diffusion or scatter, while in the second mode of illumination the light adjusting components allow passage of light therethrough with relatively high diffusion or scatter so that light emanating from the one or more illuminators is scattered in a plurality of oblique rays towards the identified anomaly, area or object of interest.

In some embodiments, the first mode of operation is characterized with a field of view (FOV) of the multi-focal optical assembly of 330°, and the first working distance of 4 to 100 mm, while the second mode of operation is characterized with a FOV of 30° to 80°, specifically of 40°, and the second working distance of 1 to 4 mm or 3 to 6 mm. In various embodiments, during the first mode of operation a magnification ranging between 100× to 6× of the captured image of the anomaly is enabled for the first working distance while during the second mode of operation the magnification available ranges between 250× to 100× for the second working distance.

Also, in some embodiments, the first mode of illumination is characterized with a field of illumination (FOI) of more than 120° with rays of illumination falling directly (also referred to as bright-field of illumination) on the anomaly. In various other embodiments, the FOI ranges between 150° and 170° in the first mode of illumination. In some embodiments, the second mode of illumination is characterized with a FOI ranging between 140° and 180° with oblique rays of illumination (also referred to as dark-field of illumination) falling on the anomaly. In certain embodiments, the second mode of illumination is characterized with a FOI ranging between 110° and 170°.

At step 1210, while navigating into the patient's colon, the at least one optical assembly is in the first mode of operation and the associated at least one type of light adjusting components are in the first mode of illumination to identify the anomaly, area or object of interest—such as a polyp. In one embodiment, the first mode of operation and illumination are enabled by default while in other embodiments a physician actuates at least one button or switch on a handle of the endoscope to trigger the processor to enable the endoscope tip section to function in the first mode of operation and illumination. The images and/or videos of the colon, during navigation, obtained by the at least one multi-focal optical assembly is displayed on at least one associated screen.

At step 1220, the endoscope tip section is moved closer to the identified anomaly (for a closer microscopic inspection using magnified viewing and imaging), the at least one optical assembly is switched or actuated into the second mode of operation and the associated at least one type of light adjusting components into the second mode of illumination to obtain a magnified image of the anomaly. In one embodiment, the physician actuates the at least one button or switch to trigger the processor to enable the endoscope tip section to function in the second mode of operation and illumination. In another embodiment, the processor is configured to automatically enable the endoscope tip section to function in the second mode of operation and illumination. In yet another embodiment, the processor is configured to enable the endoscope tip section to automatically function in the second mode of illumination once the tip section is enabled in the second mode of operation by the physician actuating the at least one button or switch on the handle of the endoscope.

At step 1230, while the at least one multi-focal optical assembly (used to optimally identify the anomaly at step 1210) and its associated at least one type of light adjusting components are enabled to function in the second mode of operation and illumination, respectively, the processor disables other optical assemblies and/or display of the other optical assemblies on corresponding screens and also disables one or more illuminators and at least one type of light adjusting components associated with the other optical assemblies (which may or may not be multi-focal and, therefore, may or may not have associated light adjusting components) when a magnification of the magnified image is over a predetermined percentage. In some embodiments, the predetermined magnification percentage is about 30% or more.

If required, a surgical tool may be inserted through a working channel of the endoscope in order to remove, treat and/or extract a sample of the anomaly or object of interest or its entirety for biopsy, while viewing the magnified image.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A tip section of an endoscope, comprising:
   a first optical assembly for generating a first image of a body cavity; and
   a second optical assembly for generating a second image of the body cavity;
   wherein the first optical assembly comprises:
      a first lens having a first depth of field and a first optical axis,
      a second lens having a second depth of field and a second optical axis, the second depth of field being different from the first depth of field, and
   wherein the first lens is movable between a first position and a second position on a path transverse to the first optical axis, wherein the first lens is movable in a first plane, and wherein the second lens is movable in a second plane different than the first plane.

2. The tip section of claim 1, wherein the first depth of field is between 3 and 100 millimeters, and the second depth of field is between 2 and 7 millimeters.

3. The tip section of claim 1, wherein the second lens is moveable between a first position and a second position on a path parallel to the path of the first lens.

4. The tip section of claim 1, wherein the first optical assembly further comprises one or more actuators configured to move the first and second lenses.

5. The tip section of claim 1, wherein the first optical assembly has a field of view of at least 90 degrees and up to 180 degrees.

6. The tip section of claim 5, wherein the first lens is positioned in an optical path of the image sensor when the first lens is in the first position, and the first lens is positioned outside of the optical path when the first lens is in the second position.

7. The tip section of claim 1, wherein the second lens has a greater magnification than the first lens.

\* \* \* \* \*